United States Patent
Akdogan et al.

(10) Patent No.: US 11,139,057 B2
(45) Date of Patent: Oct. 5, 2021

(54) DISPENSABLE UNIT RETRIEVAL MECHANISM

(71) Applicant: Hero Health, Inc., New York, NY (US)

(72) Inventors: Kutadgu Akdogan, New York, NY (US); Christian Von Heifner, Brooklyn, NY (US); Maya Kelley, Menlo Park, CA (US); Greggory Paul Hagopian, Brooklyn, NY (US); Kalyan C. Vepuri, Newtown, PA (US)

(73) Assignee: Hero Health, Inc., New York, NY (US)

( * ) Notice: Subject to any disclaimer, the term of this patent is extended or adjusted under 35 U.S.C. 154(b) by 13 days.

(21) Appl. No.: 16/824,098

(22) Filed: Mar. 19, 2020

(65) Prior Publication Data

US 2020/0216211 A1 Jul. 9, 2020

Related U.S. Application Data

(63) Continuation of application No. 16/137,265, filed on Sep. 20, 2018, now Pat. No. 10,633,135, which is a
(Continued)

(51) Int. Cl.
*B65B 35/18* (2006.01)
*G16H 20/13* (2018.01)
(Continued)

(52) U.S. Cl.
CPC ............ *G16H 20/13* (2018.01); *A61J 7/0481* (2013.01); *B25J 9/026* (2013.01); *B25J 9/1697* (2013.01);
(Continued)

(58) Field of Classification Search
CPC .............................. B66C 1/02; H01L 21/6838
(Continued)

(56) References Cited

U.S. PATENT DOCUMENTS 3,224,634 A 12/1965 Semsch
3,998,356 A 12/1976 Christensen et al.
(Continued)

FOREIGN PATENT DOCUMENTS

CN 105407857 3/2016
DE 102011112953 3/2013
(Continued)

OTHER PUBLICATIONS

EPO, "EP Application Serial No. 15830466.7, Communication Pursuant to Article 94(3) dated Aug. 14, 2019", 8 pages.
(Continued)

*Primary Examiner* — Saul Rodriguez
*Assistant Examiner* — Willie Berry, Jr.
(74) *Attorney, Agent, or Firm* — The Marbury Law Group, PLLC

(57) ABSTRACT

A system enables management of dispensable units by supporting functions such as retrieval, scheduled distribution, analysis, and notifications. To this end, a dispensable retrieval mechanism may be programmed to carry out blind retrievals of dispensable units using a retrieval strategy with a predetermined sequence of retrieval attempts (e.g., fixed or varying two-dimensional retrieval patterns), which may be open loop or closed loop. Techniques may also include the identification of dispensable units through optical sensors and weight measurement devices that can detect, e.g., a texture, a shape, and a size of dispensable units. Such identification can be used to program retrieval attempts by a retrieval robot and in the formulation of the retrieval pattern. Additionally, networked notification systems for dispensable units can be used for updating rules or schedules related to the dispensable units, or alerting users and remote resources of any potential misuse or hazards of the dispensable units.

18 Claims, 10 Drawing Sheets

Related U.S. Application Data continuation of application No. 14/819,054, filed on Aug. 5, 2015, now Pat. No. 10,106,283.

(60) Provisional application No. 62/033,498, filed on Aug. 5, 2014.

(51) Int. Cl.

| | |
|---|---|
| *B65B 35/06* | (2006.01) |
| *B65B 35/34* | (2006.01) |
| *B65B 57/14* | (2006.01) |
| *B25J 15/06* | (2006.01) |
| *B25J 9/02* | (2006.01) |
| *B25J 13/08* | (2006.01) |
| *B25J 19/02* | (2006.01) |
| *B65G 47/91* | (2006.01) |
| *G07F 11/16* | (2006.01) |
| *G07F 17/00* | (2006.01) |
| *B25J 9/16* | (2006.01) |
| *B65B 57/20* | (2006.01) |
| *A61J 7/04* | (2006.01) |
| *G05B 15/02* | (2006.01) |
| *B65B 5/08* | (2006.01) |
| *A61J 7/02* | (2006.01) |
| *B65G 65/36* | (2006.01) |

(52) U.S. Cl.
CPC ............ *B25J 13/08* (2013.01); *B25J 15/0683* (2013.01); *B25J 19/023* (2013.01); *B65B 5/08* (2013.01); *B65B 35/06* (2013.01); *B65B 35/18* (2013.01); *B65B 35/34* (2013.01); *B65B 57/14* (2013.01); *B65B 57/20* (2013.01); *B65G 47/912* (2013.01); *G05B 15/02* (2013.01); *G07F 11/165* (2013.01); *G07F 17/0092* (2013.01); *A61J 7/02* (2013.01); *B65G 65/36* (2013.01); *B65G 2201/047* (2013.01); *Y10S 901/09* (2013.01); *Y10S 901/47* (2013.01)

(58) Field of Classification Search
USPC .............................................. 414/627, 752.1
See application file for complete search history.

(56) References Cited

U.S. PATENT DOCUMENTS

| | | | |
|---|---|---|---|
| 4,047,635 | A | 9/1977 | Bennett et al. |
| 4,402,425 | A | 9/1983 | Von Schuckmann et al. |
| 4,695,954 | A | 9/1987 | Rose et al. |
| 4,712,460 | A | 12/1987 | Story et al. |
| 4,782,980 | A | 11/1988 | Heimlich et al. |
| 4,854,478 | A | 8/1989 | Gyimothy |
| 5,240,139 | A | 8/1993 | Chirnomas |
| 5,472,113 | A | 12/1995 | Shaw et al. |
| 5,490,610 | A | 2/1996 | Pearson et al. |
| 5,502,944 | A | 4/1996 | Kraft et al. |
| 5,559,503 | A | 9/1996 | Blahut |
| 5,571,258 | A | 11/1996 | Pearson |
| 5,597,995 | A | 1/1997 | Williams et al. |
| 5,646,912 | A | 7/1997 | Cousin et al. |
| 5,755,357 | A | 5/1998 | Llber et al. |
| 5,791,515 | A | 8/1998 | Khan et al. |
| 5,941,363 | A | 8/1999 | Partyka et al. |
| 6,004,020 | A | 12/1999 | Bartur et al. |
| 2,018,515 | A | 1/2000 | Sorber et al. |
| 6,142,337 | A | 11/2000 | Schreckenberg et al. |
| 6,253,955 | B1 | 7/2001 | Bower et al. |
| 6,367,473 | B1 | 4/2002 | Kafer et al. |
| 6,371,297 | B1 | 4/2002 | Cha |
| 6,411,567 | B1 | 6/2002 | Niemiec et al. |
| 6,471,087 | B1 | 10/2002 | Shusterman |
| 6,507,275 | B2 | 1/2003 | Romano et al. |
| 6,529,801 | B1 | 3/2003 | Rosenblum |
| 6,604,019 | B2 | 8/2003 | Ahlin et al. |
| 6,662,081 | B1 | 12/2003 | Jacober et al. |
| 6,685,678 | B2 | 2/2004 | Evans et al. |
| 6,732,884 | B2 | 5/2004 | Topliffe et al. |
| 6,805,259 | B2 | 10/2004 | Stevens et al. |
| 6,892,941 | B2 | 5/2005 | Rosenblum |
| 6,948,634 | B2 | 9/2005 | Evans et al. |
| 7,006,894 | B2 | 2/2006 | De La Huerga et al. |
| 7,073,685 | B1 | 7/2006 | Giraud et al. |
| 7,080,755 | B2 | 7/2006 | Laliberte et al. |
| 7,155,306 | B2 | 12/2006 | Haitin et al. |
| 7,170,823 | B2 | 1/2007 | Fabricius et al. |
| 7,198,172 | B2 | 4/2007 | Lintell et al. |
| 7,253,411 | B2 | 8/2007 | Kaushal et al. |
| 7,382,263 | B2 | 6/2008 | Danowski et al. |
| 7,395,214 | B2 | 7/2008 | Shillingburg |
| 7,404,500 | B2 | 7/2008 | Marteau et al. |
| 7,471,993 | B2 | 12/2008 | Rosenblum |
| 7,587,259 | B2 | 9/2009 | Berg et al. |
| 7,715,277 | B2 | 5/2010 | De La Huerga |
| 7,755,478 | B2 | 7/2010 | Niemiec et al. |
| 7,774,097 | B2 | 8/2010 | Rosenblum |
| 7,831,336 | B2 | 11/2010 | Gumpert et al. |
| 7,844,361 | B2 | 11/2010 | Jean-Pierre |
| 7,885,725 | B2 | 2/2011 | Dunn et al. |
| 7,887,757 | B2 | 2/2011 | Chan et al. |
| 7,944,342 | B2 | 5/2011 | Sekura |
| 7,978,564 | B2 | 7/2011 | De La Huerga |
| 7,996,106 | B2 | 9/2011 | Ervin et al. |
| 8,014,232 | B2 | 9/2011 | Niemiec et al. |
| 9,501,887 | B2 | 11/2016 | Berg |
| 2001/0002448 | A1 | 5/2001 | Wilson et al. |
| 2002/0032582 | A1 | 3/2002 | Feenery, Jr. et al. |
| 2002/0070227 | A1 | 6/2002 | Ferruccio et al. |
| 2002/0147526 | A1 | 10/2002 | Siegel et al. |
| 2002/0149472 | A1 | 10/2002 | Roe et al. |
| 2002/0169635 | A1 | 11/2002 | Shillingburg et al. |
| 2003/0099158 | A1 | 5/2003 | De La Huerga et al. |
| 2004/0054436 | A1 | 3/2004 | Haitin et al. |
| 2004/0155780 | A1 | 8/2004 | Rapchak et al. |
| 2005/0098576 | A1 | 5/2005 | Fenton et al. |
| 2005/0230409 | A1 | 10/2005 | Von Schuckmann |
| 2005/0240305 | A1 | 10/2005 | Bogash et al. |
| 2006/0058724 | A1 | 3/2006 | Laliberte et al. |
| 2006/0213921 | A1 | 9/2006 | Abdulhay et al. |
| 2007/0007301 | A1 | 1/2007 | Kaplan et al. |
| 2007/0088461 | A1 | 4/2007 | Haitin et al. |
| 2007/0093932 | A1 | 4/2007 | Abdulhay et al. |
| 2007/0156282 | A1 | 7/2007 | Dunn et al. |
| 2007/0215634 | A1 | 9/2007 | Levin et al. |
| 2008/0093371 | A1 | 4/2008 | Ubidia et al. |
| 2008/0114490 | A1 | 5/2008 | Jean-Pierre et al. |
| 2008/0140251 | A1 | 6/2008 | Handfield et al. |
| 2008/0300719 | A1 | 12/2008 | Duke |
| 2009/0069742 | A1 | 3/2009 | Larsen |
| 2009/0108016 | A1 | 4/2009 | Brown et al. |
| 2009/0134181 | A1 | 5/2009 | Wachman et al. |
| 2009/0167531 | A1 | 7/2009 | Ferguson |
| 2009/0182582 | A1 | 7/2009 | Hammon |
| 2009/0195648 | A1 | 7/2009 | Namineni et al. |
| 2009/0259336 | A1 | 10/2009 | Ratnakar et al. |
| 2009/0283538 | A1 | 11/2009 | Collins et al. |
| 2009/0581657 | | 11/2009 | Gak et al. |
| 2009/0295575 | A1 | 12/2009 | Kennedy et al. |
| 2009/0299522 | A1 | 12/2009 | Savir et al. |
| 2010/0042255 | A1 | 2/2010 | Boutin et al. |
| 2010/0076595 | A1 | 3/2010 | Nguyen |
| 2010/0084420 | A1 | 4/2010 | Van Den Broek et al. |
| 2010/0096399 | A1 | 4/2010 | Ratnakar |
| 2010/0100237 | A1 | 4/2010 | Ratnakar |
| 2010/0193579 | A1 | 8/2010 | Becket et al. |
| 2010/0228567 | A1 | 9/2010 | Wulf et al. |
| 2010/0242595 | A1* | 9/2010 | Paine ................... G01F 23/0038 73/304 C |
| 2010/0256808 | A1 | 10/2010 | Hui |
| 2010/0268380 | A1 | 10/2010 | Waugh et al. |
| 2010/0270257 | A1 | 10/2010 | Wachman et al. |
| 2010/0305749 | A1 | 12/2010 | Coe |

(56) References Cited

U.S. PATENT DOCUMENTS

| | | |
|---|---|---|
| 2010/0318218 A1 | 12/2010 | Muncy et al. |
| 2011/0060448 A1 | 3/2011 | Gotou et al. |
| 2011/0060457 A1 | 3/2011 | De Vrught et al. |
| 2011/0160896 A1 | 6/2011 | Kim |
| 2011/0166700 A1 | 7/2011 | Dunn |
| 2011/0251850 A1 | 10/2011 | Stephens |
| 2012/0006708 A1 | 1/2012 | Mazur |
| 2012/0041778 A1 | 2/2012 | Kraft et al. |
| 2012/0044054 A1 | 2/2012 | Hussain et al. |
| 2012/0101630 A1 | 4/2012 | Daya et al. |
| 2012/0199650 A1 | 8/2012 | Horst et al. |
| 2012/0316897 A1 | 12/2012 | Hanina et al. |
| 2012/0323360 A1 | 12/2012 | Lavin |
| 2012/0330460 A1 | 12/2012 | Henderson et al. |
| 2013/0006652 A1 | 1/2013 | Vahlberg et al. |
| 2013/0008918 A1 | 1/2013 | Cronin et al. |
| 2013/0060566 A1 | 1/2013 | Shavelsky et al. |
| 2013/0047986 A1 | 2/2013 | Goede et al. |
| 2013/0110283 A1 | 5/2013 | Baarman et al. |
| 2013/0134178 A1 | 5/2013 | Lu et al. |
| 2013/0238118 A1 | 9/2013 | Haas |
| 2013/0238119 A1 | 9/2013 | Simmons et al. |
| 2013/0304255 A1 | 11/2013 | Ratnakar et al. |
| 2014/0007806 A1 | 1/2014 | Stanton et al. |
| 2014/0025199 A1 | 1/2014 | Berg et al. |
| 2014/0236351 A1 | 8/2014 | Hyde et al. |
| 2014/0263391 A1 | 9/2014 | Akdogan et al. |
| 2014/0263425 A1 | 9/2014 | Akdogan et al. |
| 2014/0267719 A1 | 9/2014 | Akdogan et al. |
| 2014/0277707 A1 | 9/2014 | Akdogan et al. |
| 2014/0277710 A1 | 9/2014 | Akdogan et al. |
| 2014/0278508 A1 | 9/2014 | Akdogan et al. |
| 2014/0278510 A1 | 9/2014 | Akdogan et al. |
| 2014/0350720 A1 | 11/2014 | Lehmann et al. |
| 2015/0090733 A1 | 4/2015 | Park |
| 2016/0039553 A1 | 2/2016 | Akdogan et al. |
| 2016/0039621 A1 | 2/2016 | Akdogan et al. |
| 2016/0042151 A1 | 2/2016 | Akdogan et al. |
| 2017/0001788 A1 | 1/2017 | Akdogan et al. |
| 2017/0096285 A1 | 4/2017 | Akdogan et al. |
| 2017/0355511 A1 | 12/2017 | Akdogan et al. |

FOREIGN PATENT DOCUMENTS

| | | |
|---|---|---|
| EP | 1087322 | 10/2001 |
| EP | 1360658 | 6/2008 |
| FR | 2788040 | 7/2000 |
| JP | 2003252389 | 9/2003 |
| JP | 2005219785 | 8/2005 |
| WO | WO 0108106 | 2/2001 |
| WO | WO2005115889 | 12/2005 |
| WO | WO2009080309 | 7/2009 |
| WO | WO2009137025 | 11/2009 |
| WO | WO2011054000 | 5/2011 |
| WO | WO2012148976 | 11/2012 |
| WO | WO 2014145218 | 9/2014 |
| WO | WO2014145274 | 9/2014 |
| WO | WO2016022714 | 2/2016 |

OTHER PUBLICATIONS

JPO, "JP Application Serial No. 2018-107369, Office Action dated Oct. 1, 2019", Japanese and English translations , 15 pages.
IP Australia, "AU Application Serial No. 2014233248, Examination Report dated Jul. 18, 2019", 3 pages.
Earosas, "Pill Dispenser Prototype Video.wmv", https://www.youtube.com/watch?v=BwP2v5Mhuf8 Aug. 18, 2011 , 1 Pages.
IP Australia, "AU Application Serial No. 2015301018, First Examination Report dated Jun. 17, 2019", 5 pages.
JPO, "JP Application Serial No. 2018-107369, Office Action dated Jun. 11, 2019", Japanese and English translations , 5 pages.
IP Australia, "CN Application No. 2014233248, Examination Report dated Apr. 3, 2019", 5 pages.
IP Australia, "AU Application No. 2014233248, Examination Report dated Jul. 21, 2018", 5 pages.
IP Australia, "AU Application No. 2014233248, Examination Report dated Oct. 25, 2018", 5 pages.
IP Australia, "AU Application No. 2014233218, Examination Report dated May 26, 2017", 2 pages.
SIPO "CN Application No. 201480027727.7, First Office Action dated Jan. 29, 2018", English and Chinese Translations, 14 pages.
EPO, "EPO Application No. 14764973.5, Examination Report dated Nov. 17, 2017", 7 pages.
EPO, "EP Application Serial No. 14764973.5 , EP Search Report dated Aug. 22, 2016", 8 pages.
EPO, "EP Application Serial No. 14765247.3, EP Search Report dated Aug. 23, 2016", 8 pages.
EPO, "EP Application Serial No. 18162398.4, Extended Search Report dated Jul. 10, 2018", 7 pages.
WIPO, "International Application Serial No. PCT/US14/029940, Preliminary Report on Patentability dated Sep. 24, 2015", 14 pages.
ISA, "International Application Serial No. PCT/US14/029940, Search Report and Written Opinion dated Oct. 28, 2014", 18 pages.
WIPO, "International Application Serial No. PCT/US14/30008, Preliminary Report on Patentability dated Sep. 24, 2015", 5 pages.
ISA, "International Application Serial No. PCT/US15/43848, Search Report and Written Opinion dated Dec. 28, 2015", 14 pages.
U.S. International Searching Aut, "International Application Serial No. PCT/US2014/030008, Search Report and Written Opinion dated Aug. 8, 2014", 7 pages.
JPO, "JP Application Serial No. 2016-503286, Office Action dated Mar. 6, 2018", English and Japanese translation , 7 pages.
JPO, "JP Application Serial No. 2016-503306, Office Action dated Feb. 6, 2018", English and Japanese Translations , 11 pages.
WIPO, "PCT Application No. PCT/US15/43848, International Preliminary Report on Patentability dated Feb. 16, 2017", 11 pages.

* cited by examiner

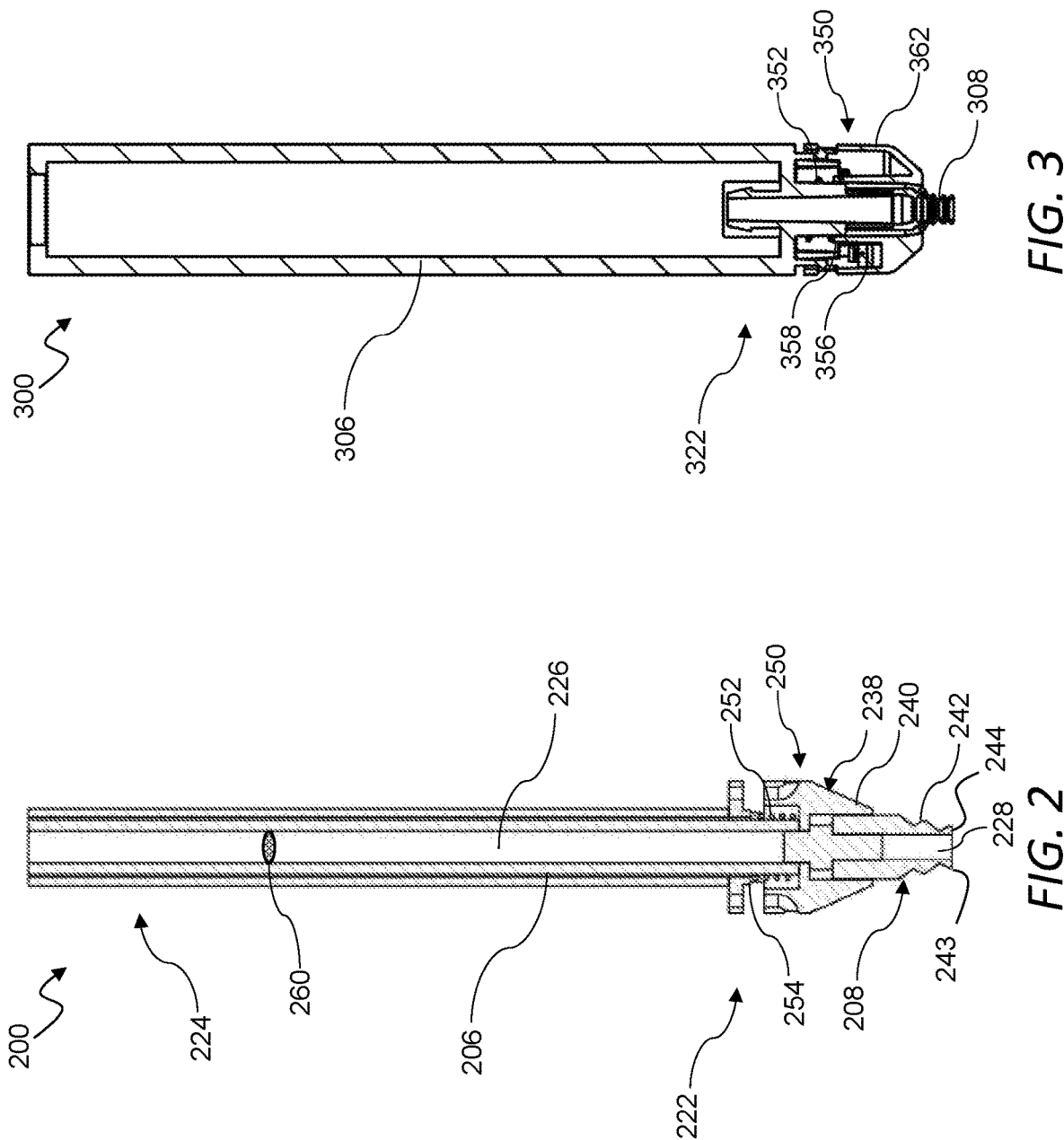

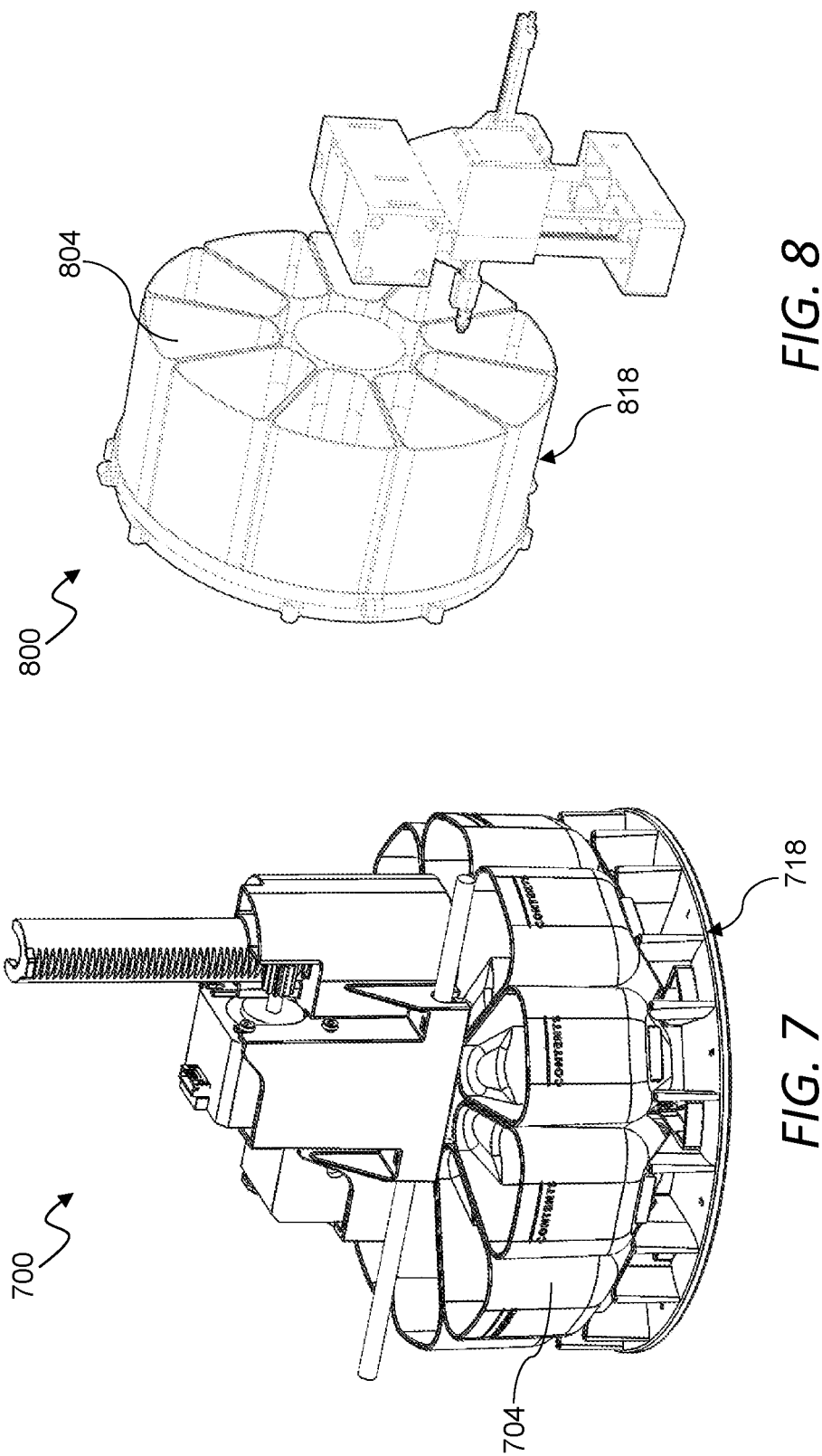

DISPENSABLE UNIT RETRIEVAL MECHANISM

RELATED APPLICATIONS

This application is a continuation of U.S. patent application Ser. No. 16/137,265, filed on Sep. 20, 2018, which is a continuation of U.S. patent application Ser. No. 14/819,054 (now U.S. Pat. No. 10,106,283), filed on Aug. 5, 2015, which claims the benefit under 35 U.S.C. § 119(e) of U.S. Provisional App. No. 62/033,498, filed on Aug. 5, 2014, with the entire contents of each of these applications hereby incorporated herein by reference.

This application is related to: U.S. patent application Ser. No. 14/214,737, filed on Mar. 15, 2014, U.S. patent application Ser. No. 14/214,779, filed on Mar. 15, 2014, U.S. patent application Ser. No. 14/214,797 (now U.S. Pat. No. 9,358,499), filed on Mar. 15, 2014, and U.S. patent application Ser. No. 14/214,828 (now U.S. Pat. No. 9,358,500), filed on Mar. 15, 2014, where the entire content of each is hereby incorporated by reference. Each of the foregoing related applications claims priority to U.S. Provisional App. No. 61/800,973, filed on Mar. 15, 2013, the entire content of which is hereby incorporated by reference.

TECHNICAL FIELD

The present disclosure relates to managing dispensable units such as health and wellness consumables, and more particularly to devices, systems, and methods for the retrieval, dispensing, management, and notification of dispensables.

BACKGROUND

There remains a need for improved techniques for retrieving and dispensing units from a mixture of one or more dispensable units of arbitrary size, orientation, texture, and weight. There also remains a need for detecting properties of dispensable units in order to facilitate dispensing, and to provide various forms of notification relating to dispensable units.

SUMMARY

A system enables management of dispensable units by supporting functions such as retrieval, scheduled distribution, analysis, notifications, and so forth. To this end, a dispensable retrieval mechanism may include a pick-and-place retrieval robot that is programmed to carry out blind retrievals of dispensable units using a retrieval strategy with a predetermined sequence of retrieval attempts such as a fixed or varying two-dimensional retrieval patterns, which may be open loop (i.e., deterministic) or closed loop (i.e., with various forms of feedback concerning results of each retrieval attempt). Techniques may also include the identification of dispensable units through optical sensors, weight measurement devices, and so forth that can detect, e.g., a texture, a shape, and a size of dispensable units. Such identification can be used to program retrieval attempts by a retrieval robot and in the formulation of the retrieval pattern. Additionally, networked notification systems for dispensable units can be used for updating rules or schedules related to the dispensable units, or alerting users and remote resources of any potential misuse or hazards of the dispensable units.

BRIEF DESCRIPTION OF THE DRAWINGS

The foregoing and other objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein.

FIG. 2 is a cross-sectional view of a retrieval arm.

FIG. 3 is a cross-sectional view of a retrieval arm.

FIGS. 7-10 show various retrieval system configurations.

DETAILED DESCRIPTION

Figure 1:
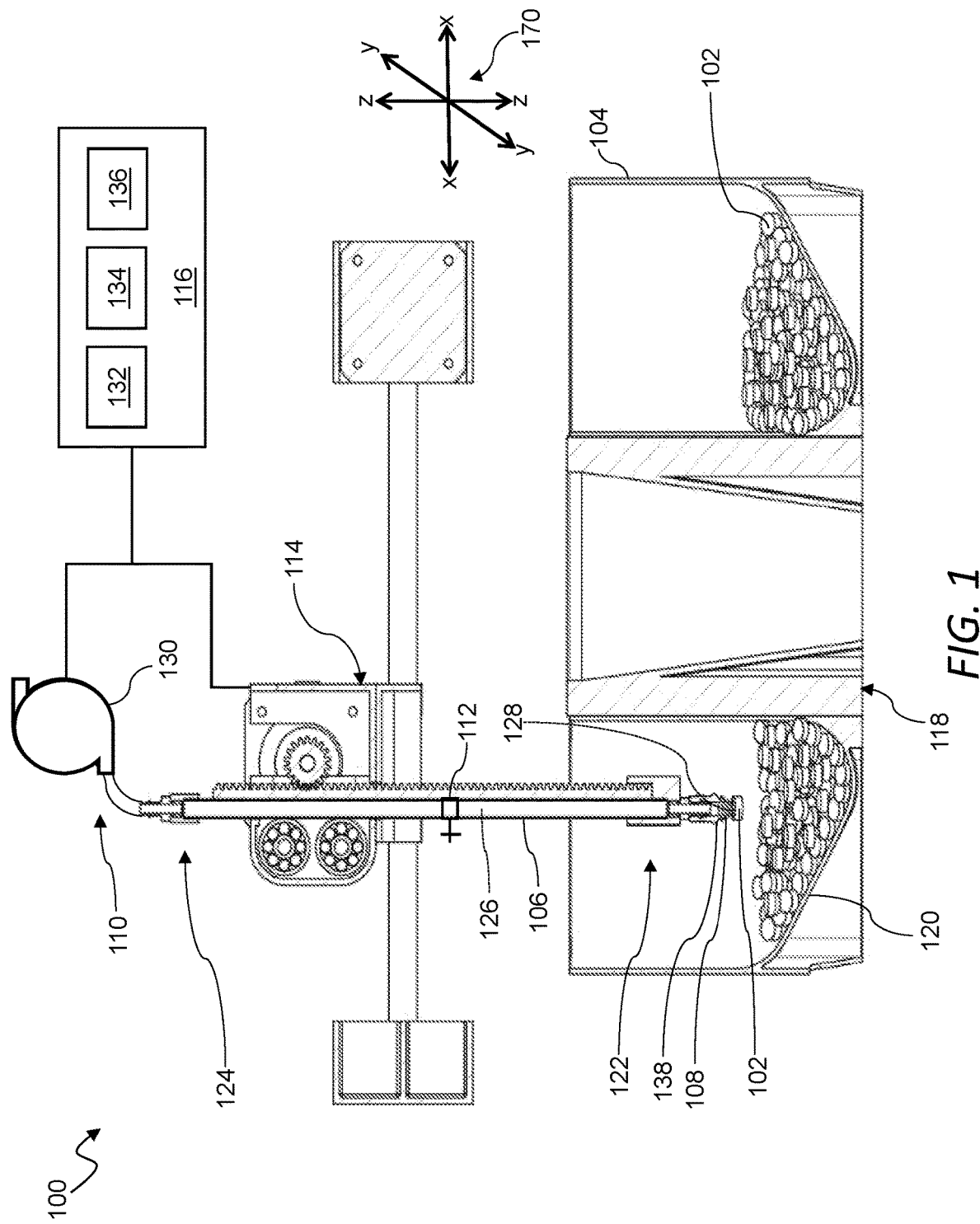
FIG. 1 is a cross-sectional view of a retrieval device.

The embodiments will now be described more fully hereinafter with reference to the accompanying figures, in which preferred embodiments are shown. The foregoing may, however, be embodied in many different forms and should not be construed as limited to the illustrated embodiments set forth herein.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "above," "below," "top," "bottom," and the like, are words of convenience and are not to be construed as limiting terms.

While the following description provides detailed embodiments of methods, systems, and devices for managing dispensable units or items, e.g., consumables, it will be understood that the specific embodiments described herein are provided by way of example and not limitation, and that various aspects of this disclosure may have additional applications independent from those that are described. For example, the systems and methods described herein may be adapted to any environment where liquids, solids, powders, suspensions, and the like are controllably dispensed on any predetermined or ad hoc schedule such as a chemical, pharmaceutical or life sciences laboratory or a packaging facility for custom deliverables. All such variations are intended to fall within the scope of this disclosure.

Definitions

The terms "item," "unit," "dispensable," and related terms such as "dispensable unit," "dispensable item," and the like, are intended to refer broadly to any item, combination of items, composition, component, material, compound, object or the like that can be dispensed in unit or continuous form.

While a "dispensable" may be any item that can be dispensed, the term "consumable" or "consumable unit" is intended to refer to dispensables that are intended to be consumed by a user. Consumables are intended to include a wide array of ingestible consumable items and form factors for same. For example, consumable units may include one or more of pills, capsules, tablets, chewables, lozenges, dissolvables, sprinkles, dissolve-in-mouth micro-capsules, orally disintegrating tablets, chewable tablets (including jelly beans, gummies, and the like), gums, and so forth, as well as continuous form consumables such as liquids or powders, solutions, pastes, suspensions, and combinations thereof. The consumables may also or instead include items provided as free powders, powder sachets, liquids, liquid sachets, vials, cups, cases, other storage forms, and so forth. More generally, the consumable units may be any composition for consumption in bulk, individual, individual pre-packaged, group pre-packaged and/or mixed item package form. For bulk form compositions, the "consumable unit" may be a predetermined portion for dispensing such as a teaspoon of liquid, a number of pills, a milligram of powder or the like, or a similar predetermined portion for dispensing or mixing into a compound locally created for dispensing prior to or after dispensing. For bulk form compositions, the "consumable unit" may be a broken or separated piece of a continuous whole (e.g., chalk).

Similarly, the content of each consumable unit may vary significantly and may include but is not limited to prescription medication, non-prescription or over-the-counter medication, nutritional supplements, vitamin supplements, mineral supplements, veterinary medications, veterinary nutritional supplements, and so forth. Consumable units may also or instead include food and other items such as sugar, seeds, candies, snacks, pet treats, or other foods and the like, as well as any other pharmaceuticals, nutraceuticals, or other consumable items not identified above. These consumables that are intended to be ingestible are also referred to herein as "ingestibles" or "ingestible units."

While consumables may include items for consumption in the conventional sense of ingestion as described above, consumables may also or instead include disposable items or the like that are intended for one time use. Thus, as used herein a "disposable" may be any consumable intended for a use other than ingestion. This may, for example, include disposable medical items such as dressings, bandages, Band-Aids, gauze, syringes, thermometers, individually packaged units of antibacterials and the like, as well as other items such as hearing aids, contact lenses and so forth that can be dispensed in individual units for one time use. This may also or instead include continuous form items not intended for ingestion including personal care items such as toothpaste, toothpicks, soap, sanitizer, moisturizer, cotton swabs and the like, as well as other household items such as glue, batteries, latex gloves, and so forth. All such disposables may be a form of consumable as those terms are used herein, and consumables may similarly be a form of dispensable.

It will be understood that while the foregoing terms (dispensable, consumable, ingestible, disposable) may be variously used in this disclosure to describe embodiments of the invention, the inventive concept generally applies to any and all such dispensables, and any description of one type of dispensable will be understood to refer to all such dispensables except where specifically noted to the contrary. Thus for example, a container for consumable items will be understood to similarly teach a container for dispensable items, a container for ingestible items, and a container for disposable items. As another example, a schedule for delivery of a medical prescription will be understood to similarly teach a schedule for delivery of any dispensable, ingestible, consumable, and disposable, with suitable modifications being readily apparent to one of ordinary skill in the art.

Another term used in the following description is "schedule." As used herein, this is intended to refer to any time-based or event-based regime for using dispensables, or more generally, any list or other arrangement of times at which possible tasks, events, or actions related to dispensables should take place or occur. This may, for example, include a single/one-off/ad-hoc trigger or time/date, or this may include any number of one time, periodic, and/or recurring events. Thus, for example, a schedule may specify an event once per day for one week, or three times a day for two weeks, or twice a day indefinitely. It will also be appreciated that a schedule may include events defined with respect to specific days or times of day, or events that are dependent on some other event. Thus for example, a schedule may indicate an event that is to occur once a day before breakfast, or three times a day after meals. While dosing regimens for medicines, nutritional supplements and the like are contemplated as schedules, it will be understood that a schedule may be provided for any dispensable contemplated herein. In general, a schedule may be a data structure stored in a memory in any suitable form for use in managing dispensables as contemplated herein, and it will be appreciated that a user may maintain any number of independent or interrelated schedules, and that a schedule may conversely specify events for any number of users, all without departing from the scope of this disclosure.

It will also be observed that a variety of terms are used to describe the hierarchical and modular structural components of a dispensable management system such as containers, cartridges, dispensers, clips, and bases. It should be understood that these are terms of convenience only and are not intended to be limiting. Instead, a wide range of system architectures are contemplated, including various distributions of processing circuitry and hardware that perform various tasks such as scheduling, notification, communications, dispensing, and so forth. Thus, for example, mechanical systems for dispensing dispensables may be integrated into a base, a dispenser, a clip, and/or a container. Similarly, processing for maintaining schedules, monitoring container contents and the like may be integrated into a base, a dispenser, a clip, and/or a container. More generally, a reference to any component of a dispensing system as contemplated herein should not be understood to require any particular hardware, processing circuitry, or functionality, and similarly should not be understood to exclude any particular hardware, processing circuitry, or functionality except where specifically stated otherwise.

In a similar fashion, a dispenser, cartridge, base, or clip may provide any level of integration with respect to containing dispensables, dispensing dispensable, managing schedules, providing notifications and so forth. At the same time, any particular function related to the managed system may be performed by a dispenser, cartridge, clip, or base, or be distributed in any useful manner among these modular components of the system. Thus the use of any one of these terms in the following description should be understood to contemplate all such devices, except where a specific form of cooperation between two such components is explicitly described.

Without limiting the generality of the foregoing, it is broadly contemplated that a container may hold dispensables in bulk or unit form. A cartridge or dispenser may house a container and provide or support dispensing functions. A base may provide a desktop unit or the like to removably and replaceably hold any number of containers, cartridges, or dispensers, and may also provide various degrees of augmentation to management of dispensables. A clip may also optionally be employed as an electromechanical interface between a base on one hand, and any container, cartridge, or dispenser on the other.

A "container," "cartridge," or the like, may be a single-dose, single-unit, multi-dose, multi-unit or continuous/burst dispensing container, which may be fully disposable, partially disposable, or fully reusable. The "container," "cartridge," or the like, may also be a housing, container, storage vessel, or the like for a plurality of units (e.g., a bulk storage container).

Dispensable Retrieval Mechanism

An implementation includes a system having a retrieval device (which may also be referred to herein as a retrieval robot, retrieval mechanism, and the like) that is a pick-and-place mechanism for consistently picking up, separating, and/or breaking apart (collectively referred to herein as "retrieving," "picking up," and the like) dispensable units from a mixture of one or more dispensable units of arbitrary size, orientation, texture, color, weight, and so forth, whether disposed in a container or otherwise. In some embodiments, the retrieval process may be referred to herein as "plunging" and the like, where a retrieval robot or component thereof is "plunged" into a dispensable unit mixture. The dispensable unit may include any degree or measurement of any physical property, including but not limited to flexibility, rigidity, malleability, elasticity, and viscosity. The mixture of one or more dispensable units may not necessarily include identical units, nor does each dispensable unit need to be identical to another dispensable unit of the same type.

The retrieval device may pick up individual dispensable units or multiple dispensable units together simultaneously or multiple dispensable units in a chain or sequence, or any combination of these. The dispensable units may be in any packaged configuration and the retrieval device may further unpackage, package, or repackage one or more dispensable units in concert with the individual or multiple unit pick-up described. Thus, while the retrieval device is described for the pick-up of individual dispensable units, it is configurable to pick up multiple units simultaneously or in a chain.

FIG. 1 is a cross-sectional view of a retrieval device. The device 100 may, in general, include machinery and control software to enable the retrieval or pickup of dispensable units 102. As discussed herein, this may include blind retrieval in which hardware performs a predetermined sequence of moves according to a retrieval strategy without any use of machine vision or other similar techniques to locate and target an item for retrieval. The blind retrieval of the dispensable units 102 may follow a variety of particular retrieval patterns as discussed herein. This may for example include open loop retrieval strategies that execute as a fixed sequence of retrieval attempts without regard to sensor feedback or the like. This may also or instead include closed loop retrieval strategies where the patterns can be adapted "on the fly" using, e.g., feedback, a machine learning algorithm, and so on. Feedback data may include, e.g., detection of contact with contents of a container where a retrieval is being attempted, detection of whether a retrieval attempt has been successful, or any other type of feedback. A so-called blind retrieval technique may use a variety of non-optical feedback sources to evaluate and update various retrieval strategies. The retrieval patterns as described herein may thus enable the device 100 to have an increased efficiency over known machine vision systems of the prior art. For example, in implementations, if the device 100 is unsuccessful in a retrieval attempt, the chances of a successful retrieval can improved on subsequent attempts by intelligently adapting the retrieval pattern on a next attempt.

The device 100 may allow for the retrieval of dispensable units 102 having any size, shape, color, texture, contour, weight, orientation, and so on. Additionally, using feedback and machine learning, the device 100 may learn improved parameters for retrieval across different types of dispensable units 102, or mixtures of dispensable units 102. Also, if the dispensable units 102 are of a known type or if they have known properties then the techniques described herein can be used to optimize the retrieval strategy accordingly. Similarly, information about containers housing the dispensable units 102 may be used to optimize retrieval. For example, the cross-sectional shape of the container through a horizontal plane of the container may help to determine an effective pattern for a series of blind retrieval attempts. Similarly, if the cross-sectional shape of the container changes along a z-axis, e.g., as retrievals are attempted deeper within the container, then this may affect retrieval strategies at each level, and at preceding levels.

The device 100 may include a container 104, a tube 106 with a nib 108, a vacuum device 110, a valve 112, a positioner 114, and a controller 116.

The container 104 may be any as described herein or otherwise known in the art for containing dispensable units 102 of the same type or of different types. The container 104 may include one or more contoured surfaces therein. The contoured surfaces may be designed such that dispensable units 102 are directed (e.g., by gravity or another force) to certain areas/volumes within the container 104, e.g., as the dispensable units 102 are being picked up by the retrieval device 100. For example, in one aspect, the bottom surface 120 of the container 104 includes contours having at least one sloped portion. In this manner, as dispensable units 102 are retrieved, units that remain in the container 104 may be guided into a known location within the container 104 for retrieval—e.g., in a vertically aligned container 104, the dispensable units 102 may be funneled down into a known location within the bottom of the container 104 through its contoured surface(s) and the force of gravity acting on the dispensable units 102. In other embodiments, another force may work to manipulate the dispensable units 102 within the container 104, e.g., a centrifugal force, a force caused by the nib 108 or other machinery, an agitation, a shaking or vibration force, and so on.

In one aspect, the container 104 is included on a carousel 118. The carousel 118 may include a plurality of containers 104, where the carousel 118 is movable for positioning at least one of the plurality of containers 104 relative to another component of the device 100, e.g., the nib 108, the tube 106, the positioner 114, and so on. For example, in an aspect, the carousel 118 is rotatable so that one of the plurality of containers 104 can be rotated into a position for engagement with the nib 108, which may itself have a limited range of motion within a horizontal plane. The carousel 118 may utilize the positioner 114 for its movement, or it may include an independent positioning mechanism. The positioning mechanism of the carousel 118 may include motors/actuators for automated movement or manual movement of the carousel 118 may be provided by a user or operator. Where one or more containers 104 are arranged around an axis of rotation of a rotatable carousel 118, the positioner 114 may achieve coverage of the entire projected surface of the container 104 with a combination of radial movement by the nib 108 and rotational movement by the carousel 118. Thus, in one aspect, general x-y positioning within a horizontal plane through one of the containers 104 can be affected through a combination of radial and rotational motion. In another aspect, the positioner 114 may provide x-y positioning coverage throughout the cross-section of a container 104, and the carousel 118 may be used to rotationally select from among a number of different available containers 104 on the carousel 118.

The tube 106 may have a first end 122 and a second end 124 coupled in fluid communication by a hollow core 126. The tube 106 may be flexible, rigid, or any combination thereof. The tube 106 may be made from one or more materials including without limitation plastic, rubber, metal, glass, ceramic, and so on. A flexible tube, e.g. made of silicone or the like, could confer space-saving advantages by folding (e.g., passive folding/unfolding or active folding/unfolding). The tube 106 may also or instead be food safe, e.g., to meet the requirements of a governing/regulating body (e.g., the Food and Drug Administration), using a material such as silicone or the like. The tube 106 may be bound flexibly, rigidly, or any combination thereof, to any wires or cables for operation of any electrical or electromechanical parts associated with the device 100. The tube 106 (and/or the nib 108) may be capable of rotating, stretching, compressing, or otherwise deforming or transforming to engage dispensable units 102 from different angles/trajectories.

The nib 108 may be disposed on the first end 122 of the tube 106. The nib 108 may include an opening 128 with a perimeter and a seal around the perimeter formed of a pliable material shaped and sized to engage and form a vacuum seal with an object having a predetermined range of dimensions, e.g., a dispensable unit 102. The nib 108 may include a bellows or the like integrated into the body of the nib 108 or the seal, which may compress and expand in a manner that imposes a predetermined range of contact forces around the perimeter of the nib 108 when contacting an object. In this manner, the contact force with a target object can be normalized to improve the vacuum seal provided around the perimeter. In one aspect, the bellows may facilitate an adaptive planar orientation of the opening 128 in order to more uniformly engage the surface of target objects, which may be in any arbitrary position and orientation within the container 104 where the nib 108 is attempting a retrieval.

Because the shape and size of the dispensable units 102 may vary (i.e., between the same type of dispensable units 102 or between a mixture of different types of dispensable units 102), the predetermined range of dimensions may be a relatively wide range of dimensions. For example, in an aspect, the nib 108 can form a vacuum seal with small units such as less than 5 mm, and larger units such as greater than 150 mm. In an aspect, the shape and size of the dispensable units 102 (including a range of shapes/sizes) is known a priori so that a suitably shaped nib 108 can be provided. In another aspect, the shape and size of the dispensable units 102 is unknown. In this aspect, the shape and size of the dispensable units 102 may be dynamically determined through techniques discussed herein.

As stated above, the nib 108 may be formed of a pliable material, including without limitation, an elastomeric material such as rubber or silicone. Regardless of material, in general, a preferred embodiment of the nib 108 is flexible and/or compressible. The nib 108 may also or instead include adhesive properties to permanently or temporarily bind to dispensable units 102, as a result of (and not limited to) one or more of the following features: pressure-sensitive tape, suction material, a suction cup, bellows, an adhesive coating, and so forth.

In an alternate embodiment, the device 100 does not include a nib 108, but rather the tube 106 retrieves the dispensable units 102 by drawing one of the dispensable units 102 through the body of the tube 106 with a vacuum force toward a desired destination.

The vacuum device 110 may include a vacuum source 130 connected in fluid communication with the second end 124 of the tube 106. The vacuum source 130 may include a vacuum pump or the like, which provides a vacuum pressure in the hollow core 126 of the tube 106 such that the nib 108 at the first end 122 of the tube 106 can draw dispensable units 102 in its immediate environment for engagement via the force provide by a pressure difference from inside the tube 106 to outside the tube 106.

In an aspect, the vacuum device 110 is capable of reversing the direction of air flow, e.g., provided by the vacuum source 130. The direction of the air flow may be reversed, for instance, using a branching line with one or more solenoid valves or using a reversible air pump. Reversing the direction of air flow may allow for the removal of any contaminants that are present (e.g., attached to a filter or the like within the tube 106) in components of the device 100, or otherwise for the removal of objects obstructing air flow in non-reversed operation of the device 100.

The valve 112 may be disposed between the nib 108 and the vacuum device 110, where the valve 112 is operable to controllably apply a vacuum force from the vacuum source 130 through the hollow core 126 to the nib 108. The valve 112 may provide for a suction state when in a first position and a releasing state when in a second position. In the first position, the valve 112 may be open, where the vacuum device 110 maintains a fluid connection with the first end 122 of the tube 106. In the second position, the valve 112 may be closed, where the valve 112 cuts off fluid communication of the vacuum device 110 and the first end 122 of the tube 106. Alternatively, the valve 112 may otherwise provide for a break in the fluid connection between the vacuum device 110 and the first end 122 of the tube 106, where a break in the fluid connection equalizes pressure within the tube 106 and its external environment. To assist with the pressure equalization and thus the speed with which the connection of a dispensable unit 102 is severed, the vacuum device 110 may be turned off at the same time as switching the valve 112 to its releasing state. Such a valve 112 may be controlled automatically, e.g., by a signal received from the controller, or manually. In an aspect, the valve 112 includes a solenoid valve or the like.

The positioner 114 may be coupled to the tube 106 and configured to move the nib 108 with at least two degrees of translational freedom within the container 104. In an aspect, the positioner 114 is able to move the nib 108 with three degrees of translational freedom within the container 104, e.g., an x-axis and a y-axis for horizontal positioning within the container 104, and a z-axis for lowering into the container 104 to attempt a retrieval at a particular x-y location. In another aspect, the positioner 114 may provide two degrees of translational freedom, e.g., an x-axis and the z-axis, while rotation of the carousel 118 provides a third degree of freedom for arbitrary positioning of the nib 108 relative to the container 104. Other arrangements may also or instead be used. For example, the carousel 118 may be vertically movable to provide a translational degree of freedom along the z-axis, or the positioner 114 may be movable radially and rotationally on an arm extending from an axis of the carousel 118. More generally, any arrangement of positioning mechanisms suitable for arbitrarily positioning the nib 108 within the coordinate system of the container 104 may be suitably employed as the positioner 114 and/or carousel 118 as contemplated herein.

The positioner 114 may include mechanical elements such as one or more actuators (e.g., linear actuators, pneumatic actuators, and so on) powered by one or more motors (e.g., stepper motors, servomotors, brushed/brushless DC motors, and so on). The positioner 114 may also or instead include any sub-mechanisms for providing movement, such as belts, pulleys, gears, threaded rods, rack and pinion systems, rails, guides, brakes, and so forth.

The positioner 114 may position one or more of the tube 106, the nib 108, the container 104, or another component of the device 100. The positioner 114 may provide for a full range of motion of the component to which it is engaged, or for limited movement, e.g., movement along one or more axes. In an aspect, the entire tube 106 is movable by the positioner 114. Additionally or alternatively, certain portions of the tube 106 may be positionable by the positioner 114 or otherwise. For example, portions of the tube 106 may be positionable by bending the tube 106 (e.g., in an embodiment where the tube 106 is flexible) or hinging the tube 106 (e.g., in an embodiment where the tube 106 is rigid). Thus, the tube 106 may include hinges, articulating joints, and the like for positioning in an embodiment. The hinges may be configured to allow the tube 106 to remain airtight, and/or to prevent kinking or closing of the tube 106. Hinging the tube 106 in this manner may be advantageous because the tube 106 can maintain suction while bending. Hinging or flexing of the tube 106 in such a manner may change a rotational orientation of the tube 106 or nib 108.

In an aspect, the positioner 114 or another component of the device 100 provides rotational movement of the tube 106. This may include a radial positioning system.

The positioner 114 or another component of the device 100 may provide for a stabilized and smooth motion of the device 100. This may be done mechanically, e.g., using bearings such as ball bearings, bearing wheels, and the like, and/or through the use of software, including but not limited to feedback controlled actuators. The positioner 114 or another component of the device 100 may also or instead allow a small or moderate amount of freedom or "wobble" in its motion, particularly in the retraction motion when retrieving a disposable unit 102. In this manner, one or more parts of the tube 106 may move freely in the horizontal plane while travelling vertically (or vice-versa). Such an embodiment may be advantageous because it can introduce noise and randomness to the position of the nib 108 during pickup of a disposable unit 102, thereby allowing new configurations of the nib 108 that can be more successful at pickup. Furthermore, such freedom may enable the first end 122 of the tube 106 to better conform to the surface of the disposable unit mixture and the surface of an individual disposable unit 102 as the first end 122 of the tube 106 moves toward this surface or unit, thus forming a tighter coupling and/or stronger seal.

In an aspect, movement of the mixture of disposable units 102 relative to the tube 106 is accomplished through movement of the container 104.

Actuating the tube 106, via the positioner 114 or otherwise, may add a significant bulk, height, or width to the device 100, regardless of whether the tube 106 is flexible or rigid. To reduce the dimensions, the device 100 or tube 106 may have one or more of the following sub-mechanisms: the tube 106 may be flexible within a scissor lift that compresses and extends for plunging; the tube 106 may be rigid but telescoping, where it extends for plunging; the device 100 may include a flexible rack attached to a flexible tube, where these components bend when in retracted positions (e.g., a flexible rack and pinion design); a chain may be attached to a flexible tube, where these components bend in in retracted positions; and so forth. The sub-mechanisms may allow for collapsing/extension in any spatial dimension or orientation, including but not limited to vertical, horizontal, and around a substantially radial or circular path. The sub-mechanisms may dynamically change the path of their collapsing/extension depending on the environment and/or enclosure. For any telescoping embodiments or the like, different sections may be included that are relatively tightly connected concentric portions. The sub-mechanisms, or components or sections thereof, may also or instead be coated with a sealant or lubricant, i.e., in an effort to preserve an airtight seal.

The positioner 114, or other components of the device 100, may be powered by alternating current (AC) power (e.g., from a grid) or direct current (DC) power (e.g., from a battery). The device 100 may have a battery backup to run the device 100 in the event of a power outage or unreliable/inconsistent power scenario. The battery may also or instead restore the device 100 to a safe or a manually overrideable state for reasons related to safety. The battery may be connected to the device 100 via a diode so that power is only drawn from the battery if a main power line voltage drops below a predetermined threshold, e.g., that of the battery (e.g., in the case where it is a lower voltage relative to a main power line).

The controller 116 may be coupled in a communicating relationship with one or more mechanical components of the device 100, e.g., the vacuum device 110, the valve 112, and the positioner 114. The controller 116 may be configured to operate the nib 108 to attempt a blind retrieval of a number of dispensable units 102 within the container 104 using a sequence of retrieval attempts each applying a different two-dimensional retrieval pattern within a first horizontal plane through the container 104. The controller 116 may also provide for the device 100 to attempt other retrieval patterns, e.g., a one-dimensional retrieval pattern and a three-dimensional retrieval pattern.

The controller 116 may include any hardware or software to provide programming as described herein. Those skilled in the art will recognize that a variety of different controllers 116 may be used in the implementations described herein.

The controller 116 may be programmable and include a network interface 132, a processor 134, a memory 136, and any other hardware or software to perform its functions as described herein.

The two-dimensional retrieval pattern used for the retrieval attempts taken by the device 100 may be determined by the controller 116, the processor 134, or another component of the device 100 (or a component in communication with the device 100, e.g., a remote device or server connected through the network interface 132). In an aspect, the two-dimensional retrieval pattern is determined based on feedback, e.g., information related to a previous retrieval attempt. This information may include without limitation whether the retrieval attempt was successful or unsuccessful, the position of the nib 108 at any point in the retrieval attempt (e.g., the position within the first horizontal plane, a z-axis position, an x-y-z coordinate, and so on), a weight of the dispensable unit 102 retrieved, a size of the dispensable unit 102 retrieved, a force exerted on the nib 108 or other component of the device 100, a location relative to the container 104 or a location within the container 104, and so forth.

The two-dimensional retrieval pattern used for the retrieval attempts taken by the device 100 may also or instead include offsetting a position of the nib 108 within the first horizontal plane by a distance greater than half of a cross-sectional width of the nib 108. The offsetting of the position of the nib 108 may first include retracting the nib 108 relative to the contents of the container 104, and then offsetting the nib 108 by a distance greater than half of a cross-sectional width of the nib 108 away from the previous retrieval attempt. In this manner, the nib 108 may be disposed in a location adjacent to its previous retrieval attempt by a distance configured to achieve a different result and/or place the nib 108 away from the epicenter of a hole created by a previous retrieval attempt. In other words, horizontally moving the nib 108 less than this distance may place the nib 108 within a hole or the like created by a previous plunge. The offsetting may also or instead include an agitating motion, i.e., moving the nib 108 a distance in the first horizontal plane to displace dispensable units 102 when the nib 108 is plunged into the container 104. Thus, agitation can be facilitated with small horizontal movements of the nib 108 (such as a half width of the nib 108 or tube 106) while inserted into the container 104.

The position of the nib 108 for an attempted retrieval within the first horizontal plane may be selected based on a variety of factors. This process of selecting positions may be parameterized along any number of different dimensions. For example, a target position of the nib 108 in the first horizontal plane for a retrieval attempt may be selected by the controller 116 based on the number of retrieval attempts in a two-dimensional retrieval pattern (e.g., at a particular height or otherwise). In general, the larger the number of retrieval attempts that are to be made within a particular horizontal plane, the more closely spaced each attempt will be to other attempts. The pattern or strategy may be determined according to this and any number of additional parameters for, e.g., separation distance between sequential retrieval attempts, time between sequential retrieval attempts, a speed of axial movement of the nib 108 (e.g., upwards or downwards), a trajectory of movement of the nib 108, a retreat margin of the nib 108, a speed of retreating of the nib 108 (e.g., above the retreat margin as described herein), a speed of approaching dispensable units 102 from a predetermined distance, an acceleration (or deceleration) while positioning the nib 108 (e.g., vertically or horizontally), a speed of horizontal movement of the nib 108, power (or a related property thereof, e.g., current) supplied to the positioner 114, power supplied to the vacuum device 110 or another component of the device 100, a pulse width modulation (PWM) frequency and duty cycle for a powered component, a property or state of the valve 112 (e.g., the length of time the valve 112 is in a released state or time the tube 106 is in an equalized or equalizing pressure state), a rigidity of the tube 106, a gear ratio of the positioner 114 (e.g., of actuators or motors contained therein), a shape of the tube 106 or a component thereof (e.g., a shape of the nib 108, which as discussed herein may be compressible), a retrieval angle of the nib 108 (e.g., a plunge angle relative to a vertical or z-axis), the size of objects for retrieval, the weight of objects for retrieval, the shape of objects for retrieval, the surface texture of objects for retrieval, the dimensions of the container 104 in which retrieval is being attempted, the shape of the container 104, supplemental capabilities of the container 104 (e.g., self-agitation to level a top surface of the objects, a stirrer to mix/level objects, ability to rotate or move within the horizontal plane, z-axis depth, etc.), and so on. Any of the above may also or instead be used as dimensions or parameters for individual retrieval attempts or patterns of retrieval attempts within a particular plane or from plane to plane. Spatial patterns may also be indexed and selected for use with a pattern parameter. For example, there may be general patterns such as parallel lines, spirals, concentric circles or other shapes, crisscrosses, random patterns, and so forth, any of which may be specified by a suitable parameter and then adapted to the shape of a container 104. Any of the above aspects of a retrieval strategy may be represented as inputs to the system, i.e., parameters that may be modified by the system for controlling the two-dimensional retrieval pattern. Specifically, these inputs may be modified to optimize the system based on the outputs described below.

The two-dimensional retrieval pattern dimensions may also or instead be determined based on, e.g., one or more of the following environmental constraints: a horizontal area covered by the dispensable unit mixture, a three-dimensional shape of the container 104 in which the dispensable unit mixture is contained, a varying height of the surface of the dispensable unit mixture (e.g., if not flat), and so forth. The environmental constraints may be constant, or they may change over time, e.g., as dispensable units 102 are retrieved.

The two-dimensional retrieval pattern used for the retrieval attempts taken by the device 100 may also or instead be determined based on one or more of: a rate of successful retrieval of dispensable units 102, a time to retrieve one dispensable unit 102, a time to retrieve a predetermined number of dispensable units 102, a noise level (measured for instance by a microphone or a human), a rate of unsuccessful retrievals, a vibration (measured for instance by a gyroscope), manual user feedback (e.g., according to user preferences), a pattern category (e.g., a random step pattern versus a pattern with a determined order of step locations), and so forth. The foregoing may represent outputs to the system, which can be measured and optimized by varying the aforementioned inputs referenced above. For example, if the rate of successful retrieval of dispensable units is low (e.g., the measured output is much less than an optimal value), one or more of the inputs may be adjusted in an attempt to raise this value, e.g., a separation distance between retrieval attempts may be increased or decreased.

The determination of pattern dimensions may occur via one or more of several methods, including but not limited to:

a manual trial-and-error of different patterns, a pre-defined, automatic "testing phase," a predetermined sequence of patterns or steps in a pattern, a machine learning process, a machine vision process, using randomization or random values, and so forth.

In an aspect, if the pattern is determined using a "testing phase," the device 100 can have a set of generic patterns preloaded into digital memory (e.g., in the memory 136 of the controller), where each of the patterns is tested and the resulting metrics after each is observed. Then, a pattern may be selected for a particular unit mixture if it optimizes the pre-defined metrics.

In an aspect, if the pattern is determined using a machine learning process, the device 100 may start with a default starting pattern, and iteratively construct a pattern with globally (or near-globally) optimal pattern dimensions (e.g., through one or more of the illustrative pattern dimension factors provided above) to optimize the pre-defined metrics, e.g., using one or multiple optimization algorithms and techniques (including but not limited to a simplex algorithm, Newton's method, finite difference, gradient descent/hill climbing, and simulated annealing). The device 100 may separately use (independently or in conjunction) one or more supervised or unsupervised learning algorithms, such as nearest neighbor, neural networks, and cluster analysis. An illustrative example of the learning process may have the following steps: (1) begin at a pre-determined default pattern (with default dimensions) for instance using a winding route or a spiral route, (2) run one or many steps of the pattern, (3) measure the pre-defined metrics m, (4) modify one of the dimensions d (e.g., a number of steps) by a small increment δd that is expected to improve the measured metric $m_i$, based on the change in $m_i$ during the previous step, (5) repeat steps 2-4, choosing a new small increment, (6) repeat steps 2-5 until this dimension is optimized within a predefined or algorithmically determined margin of error $\xi_d$ for that dimension, (7) move to another dimension, and optimize via steps 2-6, holding the other dimension constant, (8) repeat steps 2-7 until optimized in all dimensions. In an aspect, δd can be a small fraction, e.g., approximately one percent of the total range of values that a dimension may take, for instance: (new_plunge_speed)=(old_plunge_speed+(max_plunge_speed×0.01)). This fraction may be empirically determined for optimality.

In an aspect, if the pattern is determined using a machine vision process, the device 100 may have one or more optical sensors or cameras (e.g., charge-coupled device (CCD), complementary metal-oxide-semiconductor (CMOS), and the like) on a top surface (or "ceiling" surface) or at the bottom of the tube 106, i.e., facing downward towards the dispensable unit mixture. Based on images generated by these sensors, a microprocessor (e.g., the processor 134 of the controller 116) may perform image recognition to determine where visible dispensable units 102 are located (e.g., by using edge detection algorithms), and direct the horizontal actuation such that the tube 106 is plunged vertically down to a center of a dispensable unit 102 that appears to have a high success rate for retrieval, which in most operations is the dispensable unit 102 that has the largest surface area exposed to the optical sensors. Furthermore, in an aspect with actuators disposed near the bottom of the tube 106, the microprocessor may also or instead direct the actuators to bend, hinge, or otherwise direct the bottom of the tube 106 towards the center of the dispensable unit 102 that appears to have a high success rate for retrieval, and which is also in range of the tube's bending or hinging. Additionally, when using the machine vision process in conjunction with the machine learning process, the image recognition may be used to determine the average dispensable unit 102 shape, size, and separation, hence informing the optimal separation between "plunges" (i.e., one of the pattern dimensions discussed above).

The device 100 may receive input from an external signal or message, indicating, for example, the following or a combination of the following: the exact pattern (i.e., pattern dimensions) to use, the default starting pattern as a beginning for the machine learning process discussed above, and the size of the small increment δd for a particular pattern dimension in the machine learning process. This input may be driven by a detection received from some other component related to an environmental constraint, including but not limited to: the average size, shape, texture, weight, and orientation of dispensable units 102 in one or more of the nearby mixtures, the ambient temperature, pressure, or humidity, and the like, or other factors or inputs. This input may come from a human or a machine, where examples of the latter include but are not limited to a server (via the internet/intranet, Ethernet, ZigBee, WiFi, 3G, 4G, LTE, WiMAX, and so forth), another processor (whether onboard the device 100 or not), a remote resource, and so forth.

Although the device 100 in the figure is shown as a vertically-aligned retrieval device, where the two-dimensional retrieval pattern is discussed as being through a horizontal plane, one skilled in the art will recognize that other alignments are also or instead possible. For example, in another aspect, the device is a horizontally-aligned retrieval device, where the two-dimensional retrieval pattern is through a vertical plane. Other alignments, e.g., tilted or angled alignments are also possible. Still more generally, while an x, y, z coordinate system 170 generally serves as a convenient basis for positioning within three dimensions and are included in some of the discussions regarding positioning herein, any other coordinate system or combination of coordinate systems may also or instead be employed, such as a positional controller and assembly that operates according to cylindrical or spherical coordinates.

Actuation and movement of components of the device 100 along any axes or any directions may be controlled or restrained by various sensing systems (which may be collectively referred to herein as "actuation sensor systems") and mechanical constructs. Such actuation sensor systems may include but are not limited to optical-interrupter-based encoders, rotary encoders, linear encoders, quadrature encoders, and the like. The actuation sensor systems may include the resolution of encoding for preferred, accurate motion, along with one or more index or "home" positions. Such actuation sensor systems may be used in conjunction with control software to drive the actuation, e.g., of motors included in the positioner 114. Mechanical constructs may include hard stops (e.g., a protruding lip) and the like. Actuation may use a combination of actuation sensor systems and mechanical constructs.

As discussed herein, motion may be relatively smooth to ensure relatively fast retrieval of dispensable units 102, a relatively high rate of retrieval success, and a durable mechanism. This may be achieved by using ball bearings, ball bearing wheels, smooth metal rods (e.g., stainless steel SS301, SS303 or SS304 with 9 micron finish or finer), Kapton tape, or similar. Some embodiments may have less smooth travel on one or more axes relative to another, e.g., for dampening motion.

The device 100 may further include an agitator 138 engaged with the first end 122 of the tube 106 that converts an axial force created by a vertical movement (i.e., plunging)

of the tube 106 or plunger into a horizontal force parallel to (or substantially parallel to) the first horizontal plane for agitation of the dispensable units 102. In other words, when the tube 106 is plunged in a direction along the z-axis, the agitator 138 may displace dispensable units 102 in which it contacts along one or more of the x-axis and the y-axis, e.g., through an x-y plane. The agitator 138 is further described below.

In general, in use, the device 100 may involve the tube 106 with the nib 108 being plunged (e.g., vertically or substantially vertically, horizontally or substantially horizontally, or otherwise) into a mixture of disposable units 102. This actuation may occur using the positioner 114 as described herein. Upon contact between the nib 108 and a disposable unit 102 (e.g., on the surface of the mixture or near the surface of the mixture), suction caused by the pressure difference between tube 106 and the external environment may draw the disposable unit 102 to the nib 108, where the nib 108 forms a sealed connection with the disposable unit 102. The disposable unit 102 may thus be held by the tube 106 due to the force of the vacuum pressure, which is selected to be sufficiently strong to keep the disposable unit 102 connected to the nib 106 against the force of the weight of the disposable unit 102 and any disturbing or resistive forces such as that imposed by other disposable units 102 nearby, heavy vibrations, movement of the nib 108 or tube 106, or otherwise.

Once the connection with the disposable unit 102 has been made, the positioner 114 may retract the tube 106 from the container 104, e.g., pull the tube 106 up along the z-axis in the vertically-aligned device shown in the figure. Due to the engagement, the disposable unit 102 may travel with the tube 106. Upon a signal, e.g., from the controller 116, the engagement may be broken, thus releasing the disposable unit 102, which may fall due to, e.g., its own weight, an artificially applied field (e.g., magnetic field), or similar. The engagement between the nib 108 and the disposable unit 102 may be broken, e.g., by turning off the vacuum source 130, by releasing a mechanical grabber, by operation of the valve 112, and the like.

FIG. 2 is a cross-sectional view of a retrieval arm. The retrieval arm 200 may be part of a retrieval device as described herein, and may include a tube 206 having a first end 222 and a second end 224, a nib 208, a hollow core 226, an opening 228, and an agitator 238. The retrieval arm 200 may otherwise be referred to herein as a plunger.

As shown in the figure, the agitator 238 may include one or more angled surfaces 240, or otherwise sloped or contoured surfaces. The angled surface 240 may be configured to displace dispensable units when the nib 208 attempts the blind retrieval as described herein. Specifically, when the retrieval arm 200 is plunged into a container of dispensable units, the angled surfaces 240 may engage with one or more of the dispensable units thereby displacing them, e.g., horizontally away from the retrieval arm 200 when the retrieval arm 200 plunges vertically. In this manner, the agitator 238 may convert an axial force created by a plunging of the tube 206 into a horizontal force within a horizontal plane (e.g., the first horizontal plane described herein) for agitation of the dispensable units.

In an aspect, the agitator 238 substantially resembles a cone or a truncated cone, which can aid in preventing damage to dispensable units by directing the units radially outward from the retrieval arm 200 when it plunges downwards.

As shown in the figure, the nib 208 may include one or more bellows 242. The bellows 242 may be formed by a substantially pleated layer of material included on the nib 208 that permits the nib 208 to be compressible. Being compressible may allow the nib 208 to conform its shape to the shape or texture of a dispensable unit, while also or instead permitting the nib 208 to absorb axial forces caused by a plunging of the tube 206. At the same time, the bellows 242 can facilitate reorientation of the seal 243 around the perimeter 244 of the opening 228 so that the plane of the seal 243 can adjust to a range of arbitrary planar orientations of the surface of objects within the container. In this manner, the nib 208 can maintain a predetermined range of contact forces around the perimeter 244 to form a desired vacuum seal when contacting objects in a range of different positions and orientations within the container. The bellows 242 may be formed of the same material that forms the nib 208 or a majority thereof, or the bellows 242 may be formed of a different material. In an embodiment, one or more of the nib 208 and bellows 242 may be formed of an elastomer, such as silicone rubber or the like, although other materials are also or instead possible. The bellows 242 may permit the seal 243 of the nib 208 to move relative to the tube 206 as the positioner moves the tube 206 vertically into the container, thereby maintaining a predetermined range of contact forces as the seal 243 of the perimeter 244 of the nib 208 contacts contents of the container. This can allow the nib 208 to absorb axial forces created through contact of the nib 208 with contents of the container or other objects/components. The bellows 242 may be further configured to normalize an axial force on the nib 208 created by a plunging of the tube 206 in order to strengthen the vacuum seal between the nib 208 and a dispensable unit.

The retrieval arm 200 may further include a biasing element 252 that works in conjunction with an indicating element 250. The biasing element 252 may movably couple the indicating element 250 to the tube 206, where the biasing element 252 biases the indicating element 250 in a direction with a predetermined biasing force. For example, in a vertically aligned retrieval device, the biasing element 252 may bias the indicating element 250 in an axial direction (along a z-axis), i.e., perpendicular to a surface formed by contents of a container. The predetermined biasing force may be selected such that a force on the tube 206 that causes compression of the biasing element 252 does not damage one or more of the tube 206 and the dispensable units. In an aspect, the indicating element 250 is engaged with the nib 208 such that the indicating element 250 moves relative to the tube 206 when a contact force applied to the nib 208 is greater than the predetermined biasing force on the indicating element 250. In one aspect, the nib 208 and the indicating element 250 may be configured such that any vertical movement of the nib 208 relative to the tube 206 also causes vertical movement of the indicating element 250. In another aspect, the nib 208 and the indicating element 250 may be configured such that the nib 208 can compress a predetermined amount before the indicating element 250 will move relative to the tube 206. This compression may be made possible by the material of the nib 208 as described herein. The retrieval device or system may further include a controller as described herein, where the controller is configured to infer contact of the nib 208 with contents of the container upon detecting a movement of the indicating element 250 relative to the tube 206. This inferred contact may indicate to the retrieval device or system that the nib 208 has contacted a surface formed by the contents of a container, thereby providing an axial position of this surface to the controller or other component of the retrieval device or system.

As shown in the figure, the indicating element 250 may be disposed on the first end 222 of the tube 206. The biasing element 252 may include a mechanical spring or the like, and/or the biasing element 252 may include an elastomeric material, e.g., of the indicating element 250 or another component of the retrieval arm 200 such as the nib 208. The biasing element 252 may utilize a mechanical stop 254 provided on the retrieval arm 200 (e.g., on the tube 206), which can counteract a contact force on the indicating element 250 or nib 208. As discussed above, a predetermined force that allows for compression of the biasing element 252 may be selected to coincide with a force exerted on the tube 206 when the first end 222 of the tube 206 contacts a plurality of dispensable units, e.g., dispensable units that form a top surface of a dispensable unit mixture in the container.

In an embodiment, the indicating element is the nib itself. In this embodiment, the biasing element may be the pliable material of the nib that allows the nib to be compressible, or the biasing element may be a separate component that movably couples the nib and the tube. In another embodiment, the indicating element 250 is coupled to the nib 208 (as shown in the figure). In yet another embodiment, the indicating element and the agitator are the same component, where the agitator is movable in an axial direction on the tube.

In an implementation in which the indicating element 250 is connected to the nib 208, the indicating element 250 may be minimally separated from the nib 208. In an aspect, the indicating element 250 is seamlessly connected to the nib 208 or is otherwise a part of the nib 208. For example, the indicating element 250 may be molded onto the nib 208. Such a connection can ensure that there is no room for contaminants or residue to travel up between the nib 208 and the indicating element 250 and therefore damage or interfere with mechanics or electronic functionality.

In an aspect, the biasing element 252 may also serve to absorb a force caused by contact between the first end 222 of the tube 206 (which may or may not have a nib 208) and a surface of the dispensable unit mixture (or a surface of the container or the like). The biasing element 252 may thus prevent the tube 206 from transferring a relatively strong force to the dispensable unit mixture (or vice-versa), which may prevent damage to one or more of the dispensable units or the tube 206.

The retrieval arm 200, or another component of the retrieval device or system, may include a filter 260. The filter 260 may prevent contaminants from entering the vacuum device through the tube 206. The filter may use active or passive filtration to remove contaminants, and may be powered or unpowered in the active filtration embodiment. A passive filter may include a filtration material (e.g., a porous cloth or plastic) and an enclosure around the filtration material to create a seal in the line in which it is disposed and ensure that air flows through the filtration material. The filtration material may be shaped in several ways, including but not limited to a disc, a cone, a cylinder, and so on.

The filter 260 may be located within the tube 206 or along another portion of the retrieval device or system. Wherever disposed, the volumes adjacent to the filter 260 may be shaped such that there is a certain predetermined volume preceding the filter 260 and a certain predetermined volume following the filter 260 (e.g., relative to the direction of flow of air in an embodiment including a vacuum device). The volume following the filter 260 may be relatively small, e.g., to ensure that there is as little recirculation of air flow as possible (which can lead to energy loss). The volume preceding the filter 260 may also or instead be relatively small to prevent similar recirculation, but it may be large enough such that any contaminants blocked by the filter 260 have space to fall or be pulled by a different force away from the filter 260, thus preventing air flow through the filter 260 from being blocked. The preceding predetermined volume may further include a trough section, situated in the direction of such a "different force" (which may be gravity, thus the trough may be situated under the filter 260 with respect to gravity), which would be disposed in a region in which contaminants could collect without substantially obstructing an air flow.

FIG. 3 is a cross-sectional view of a retrieval arm. The retrieval arm 300 may be an alternate embodiment of the retrieval arm discussed above. In this embodiment, the indicating element 350 may work in conjunction with a sensor 356 and guide rails 358.

In one aspect, the sensor 356 is configured to detect movement of the indicating element 350 relative to the tube 306 and to send a signal to a controller when the movement is detected. Upon receiving the signal that movement of the indicating element 350 relative to the tube 306 is detected, the controller may be configured to halt or reverse axial movement of the nib 308 within the container. This may prevent damage to one or more of the dispensable units and the tube 306 by terminating a downward motion of the tube 306 and nib 308 upon contact with objects within a container, or more specifically, when the contact force between the nib 308 and the objects exceeds a predetermined threshold governed by a spring constant or the like of the biasing element 352.

The sensor 356 may include an optical-interrupter sensor or the like. For example, upon compression of the biasing element 352, a light-blocking and/or reflective protrusion or the like may move into a path of the optical-interrupter sensor, thus triggering a signal that the first end 322 of the tube 306 has touched the surface of the dispensable unit mixture. This protrusion may be made of metal (e.g., stainless steel) for optimal interrupting in the environment within the retrieval device, where such an environment can include air, dust, residue, and other materials or contaminants that might be present in the gap between an optical-interrupter.

In another aspect, the sensor 356 includes electrical contacts that are separated at rest, e.g., in the absence of external forces, and that come into contact with one another upon compression of the biasing element 352. Such contact may complete a circuit, thereby transmitting an analog or digital signal to a controller, which would thus determine that the first end 322 of the tube 306 has touched the surface of the dispensable unit mixture (with a predetermined contact force sufficient to overcome the biasing force of the biasing element 352). In such an embodiment, the first end 322 of the tube 306 may be electrically insulated to prevent a completion of the circuit when at rest (i.e., when the biasing element 352 is not compressed), thus preventing transmission of an incorrect signal. The biasing element 352 and contacts may also or instead reside entirely within a mechanical switch or the like. Numerous other contact sensors and systems are known in the art, and may be adapted for use with the retrieval arm 300 contemplated herein.

Information provided by the indicating element 350 or another component of the retrieval arm 300 or retrieval system may be stored, e.g., in a memory or database that is coupled in a communicating relationship with the controller (or disposed in the controller itself). In an aspect, the memory may store a position of the nib 308 (e.g., an axial position) where movement of the indicating element 350 relative to the tube 306 is detected. This may be a z-axis or vertical axial position that corresponds to a top surface of the plurality of dispensable units within the container. This may also or instead include a horizontal or x-y position at which the contact was detected. The controller may then be configured to position the nib 308 for a retrieval attempt in the two-dimensional retrieval pattern at a predetermined height. The predetermined height may be disposed above the surface of the plurality of dispensable units within the container such that the nib 308 will not contact the dispensable units until making a retrieval attempt and will thereby not be hindered by the dispensable units. The predetermined height may also be disposed relatively close to the surface of the plurality of dispensable units, such that the time when retracting the nib 308 (e.g., after an unsuccessful retrieval attempt) is reduced.

Thus, in an aspect, in order to compensate for a vertically uneven disposable unit mixture, the system may store, record, extrapolate, or otherwise capture or calculate the depth or "level" at which it previously encountered a dispensable unit, which may be equivalent to the surface level of the mixture at that horizontal coordinate. This information may be advantageously employed in a number of ways when determining a retrieval pattern or strategy. For example, this information may be used to prevent horizontal movement of the nib 308 into dispensable units that might damage the retrieval arm 300. This may also be used to avoid damaging dispensable units through excessive vertical motion or dragging across a top surface of the units within a container. In another aspect, this information may be used to select a specific z-axis position where a next retrieval will be attempted, either within the neighborhood of the contact detection or at other locations within the container. Thus, the system may record a surface level at several horizontal coordinates, and may use this information to map or estimate the surface level throughout the container. With such information, the mechanism could retreat to a safe vertical position that is a certain distance (i.e., a "retreat margin") above the surface of the dispensable units at the next pattern location, and could thus move to that new elevated position without striking dispensable units horizontally. Furthermore, to increase the speed of the entire process, the retrieval arm 300 may establish a separation margin—a minimum distance between the nib 308 and the expected surface height—as a rule to be followed before horizontal movements. Thus, the amount of z-axis movement may be reduced or eliminated to save time during and between retrieval attempts.

The sensor 356 may also or instead work in conjunction with, or be replaced by, other sensors or distance-controlled motors, including but not limited to, Hall effect sensors, rotary encoders, linear encoders, linear actuators, stepper motors, and so on. In this manner, the retrieval mechanism may be used to inform the controller of the depth distance of the surface of the dispensable unit mixture at the tube's current horizontal coordinates, depending on the distance traveled before the sensor 356 (or otherwise) was activated.

Further examples of other sensors that may be utilized include without limitation optical sensors (e.g., for computer-aided counting of surface and sub-surface dispensable units), motion sensors (e.g., for accurate depth readings), porosity sensors, acoustic resonator/sensors (e.g., for depth and volume readings), humidity sensors, temperature sensors, and so on. Adaptations of these embodiments may place described sensors anywhere within the described device or system, for instance within the containers.

The guide rails 358 may provide for movement of the indicating element 350 or a component thereof, e.g., in the axial direction. The guide rails 358 may also or instead prevent unwanted movement of the indicating element 350 or a component thereof, e.g., in the horizontal direction.

The retrieval arm 300 may also include a cover 362 that protects components disposed therein. These components may include, e.g., the sensor 356, the biasing element (e.g., a spring), the guide rails 358, and so forth. The cover 362 may be particularly advantageous to prevent build-up of material from the dispensable unit mixture on an optical-interrupter sensor or the like.

Any of the devices and systems described above may also include other advantageous control features, e.g., provided by a processor within a controller or the like. For example, a processor may estimate the number of dispensable units remaining in a container, for example using calculations based on one or more of: (1) a vertical location of the surface of the dispensable unit mixture at one or more horizontal coordinates, (2) a depth of the dispensable unit mixture at one or more horizontal coordinates along the surface of the dispensable unit mixture, (3) the depth of the container at the horizontal coordinates where there are no dispensable units in the container (this may be a known property of the container), and (4) dispensable unit characteristics (e.g., based on the pattern dimensions determined as described herein), which can allow for the calculation of average density of the dispensable units.

All information, data, calculations and measurements contemplated herein (including but not limited to machine learning data and sensor data) may be stored in a database, displayed to a user, transmitted locally (e.g., to other integrated circuits) or remotely (e.g., to a server), or further processed. All data, for instance machine learned pattern dimensions, may have local values (i.e., within the mechanism) and global values (e.g., at a remote, central location, such as a server). The global values may be communicated to multiple devices or systems that may or may not be in proximity, and then such mechanisms can combine their existing local values with the received global values to calculate a new blended set of local values that could be used for processing or storage in a database, communication to a user, or any other data use described herein. In this manner, data for one device may be used to improve operation of other, similar devices performing similar dispensing operations, and new devices may be quickly optimized according to historical performance of similar devices. This sharing of operational parameters and other information may be automated through a centralized network resource or a peer-to-peer network among devices, or this sharing may be partially automated such as where information is curated or otherwise managed with human oversight before sharing among different machines through a network resource. In another aspect, users may manually select information or parameters from a central repository that is available as a network resource.

All mechanical and sensor subsystems, in conjunction with some or all electronics and processing capabilities in the software, may together form a control system that regulates the mechanism to improve accuracy and reduce or avoid errors. Such a control system may also protect against single fault conditions, e.g., where any single electromechanical or software issue caused externally does not result in unsafe or unacceptable operation, or does not result in an error state.

The control system may also or instead include a pressure sensor, a level indicator (e.g., as described herein), a hard stop (e.g., a protruding lip or the like) at one or more ends of the plunger mechanism or tube, and a sensor at an opposite end thereof. The pressure sensor may be able to detect whether a dispensable unit has been retrieved, as retrieving a unit and forming a full seal in the vacuum line would result in a drop of pressure below that of the environment outside the mechanism, i.e., a drop measurable by the pressure sensor. The pressure sensor may further be used to inform depth distance in conjunction with or replacement of the level indicator described herein. Such a control system may enable the plunger to: plunge vertically downwards until the pressure sensor indicates that a dispensable unit has been retrieved or until the level indicator indicates that the plunger has collided unsuccessfully with the dispensable unit mixture; and to retreat to a safe distance, but no further than a hardstop lip, and no further than indicated by the sensor on the opposite end of the plunger or tube. Thus, the position may be determined between certain known endpoints, and the plunger would be much less likely to damage or exert excessive force onto the dispensable unit mixture given this known position.

The control systems described herein may employ a state machine, such that there are states for normal operation and states for particular or groupings of errors, for example, a state where actuation has been jammed. The state machine may be configured as a directed graph such that a fault results in an observable error state and the device does not remain in a normal operation state when in this condition.

The control system may be activated or manipulated via a user interface on a user device. The user interface may include a touchscreen. The user device may include any known in the art, e.g., a computing device (e.g., a smart phone, a tablet, a PDA, and so on), a computer, a watch, and so on. The user device may also or instead include a connected or synchronized accessory.

The mechanisms described herein may be able to detect when a dispensable unit has been dropped into a drop zone, retrieval area, or designated chute (e.g., via a pressure sensor that detects when the vacuum line is no longer sealed). Further, the mechanisms may be able to detect when a dispensable unit has fallen into a desired rest state or dispensing vessel, or when such a dispensing vessel has been removed. Such detection may occur using a light emitting source (e.g., an infrared light-emitting diode (LED)) on one side of such a vessel and a phototransistor on the other side. The phototransistor may be able to detect the presence (or absence) of such a vessel based on light passing into the phototransistor. Improving the accuracy of the reading may be achieved by sending an amplitude-modulated signal from the LED (at a particular frequency or set of frequencies) and taking a Fast Fourier Transform (FFT) of the response of the phototransistor—this can make the measurement far less susceptible to noise or environmental factors such as direct sunlight.

The mechanisms described herein may also include food safe components, and may for instance comply with regulatory food safety requirements. Illustrative materials suitable for food safe containers include polycarbonate, polypropylene, or the like for permanent contact with food-related substances, or acrylonitrile butadiene styrene (ABS) or the like for temporary contact with such substances.

The mechanisms described herein may be part of, or form, a modular system. The modular system may include, e.g., an operating system, a user interface, containers, retrieval devices, dispensable unit mixtures, chutes, carousels, and so forth. Such a modular design facilitates maintenance and repair, as well as reliable design, and simple extension or expansion of the system.

The mechanisms described herein may be stationary or handheld/portable. In a portable embodiment, the mechanisms may be bridged to separate actuation mechanisms, e.g., a car, a helicopter, a drone, and the like, which may allow for dispensing of onboard dispensable unit mixtures (e.g., drone-delivered medical supplies) or pickup and dispensing of dispensable units into certain environments (e.g., mining).

Figure 4:
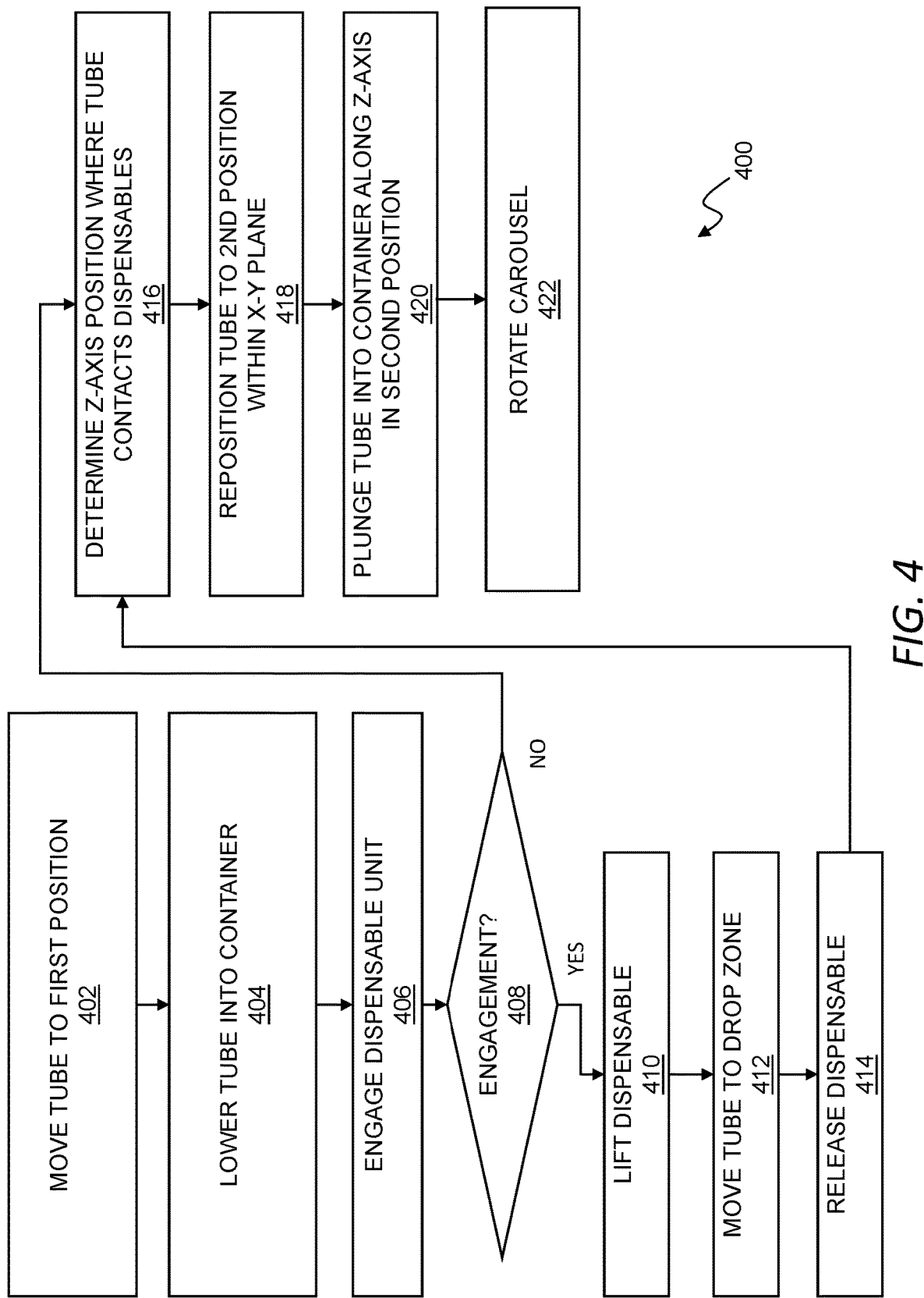
FIG. 4 is a flow chart of a method for retrieval of dispensable units.

FIG. 4 is a flow chart of a method for retrieval of dispensable units.

As shown in step 402, the method 400 may include positioning a tube in a first position in an x-y plane for cooperation with a container including a plurality of dispensable units. The first position may be any position selected according to a retrieval pattern or retrieval strategy as contemplated herein. For example, this may include a position determined by a predetermined pattern such as a particular geometric pattern, a combination of patterns, a random pattern, or any combination of these. The position may also or instead be dynamically adjusted according to feedback from sensors concerning, e.g., surface height, retrieval success, container weight, and so forth. The position may instead be a random position.

As shown in step 404, the method 400 may include moving the tube into the container along a z-axis in the first position such that a first end of the tube contacts one or more of the plurality of dispensable units. In one aspect, the tube may stop as soon as contact is detected. In another aspect, the tube may drive into the container with a force selected to displace one or more of the plurality of dispensable units. Thus, the tube or nib may be forcibly directed into the container in order to slightly agitate or mix the dispensable units within the container. Thus, the nib or other components of the tube may operate as an agitator to periodically normalize the distribution of dispensable units within the container. In another aspect, the tube may be moved slightly within a horizontal plane while inserted into the dispensable units in order to actively stir the contents.

As shown in step 406, the method 400 may include actuating an engagement mechanism to create an engagement between the first end of the tube and one of the dispensable units. The engagement mechanism may include a vacuum force exerted through an opening in a nib on the first end of the tube, a mechanical grabber, and so forth. For example, in one aspect, in addition to or lieu of a vacuum device, the device may use an articulating claw, grasper, or other electromechanical device suitable for retrieving dispensable units.

As shown in step 408, the method 400 may include determining whether engagement between the first end of the tube and the dispensable unit is achieved. Determining whether the engagement is achieved may include the use of one or more sensors, e.g., optical sensors, pressure sensors, weight sensors, force sensors, contact sensors, and so on. If engagement is achieved the method 400 may move onto step 410, and if not, the method 400 may move onto step 416 or another step in the method 400, such as step 418. It will be appreciated that engagement may be tested at other times during the process 400. For example, the retrieval device may be simplified by foregoing any detection sensors or electronics on the tip of the retrieval device, and a retrieval attempt may be deterministically completed (e.g., by moving to a drop zone and performing a release) without regard to whether a dispensable unit has been retrieved. The success can then be tested at the drop zone in order to suitably update the retrieval pattern.

As shown in step 410, the method 400 may include lifting the dispensable unit, e.g., by moving the tube along the z-axis or otherwise operating the retrieval device to move the dispensable unit vertically from the mixture. For example, the tube may be retracted in a direction normal to the surface of the dispensable unit mixture, or it may be retracted at an angle relative to the surface of the dispensable unit mixture, or the tube may include an actuator or the like to raise the nib without moving the tube or other components of the retrieval device.

As shown in step 412, the method 400 may include moving the tube until the dispensable unit is disposed within a predetermined drop zone. This may, for example, include moving the tube along the x-y plane substantially perpendicular to the z-axis until a desired horizontal position is reached, or moving in any combination of x, y, and z steps to navigate the end of the tube to a desired location. For example, moving the tube may also be accomplished at an angle or other trajectory that includes movement along all three axes, or alternatively, the z-axis and at least one of the x-axis and y-axis. The drop zone, also referred to herein as a "release zone," "release area," or the like, may be a specific horizontal region without regard to height, or the drop zone for the dispensable unit may more specifically be the horizontal region at a specific height, or at a range of heights that bound a volume within which the dispensable unit may be released by the retrieval device. The drop zone may also include hardware or the like to receive the released item and/or direct the released item toward a retrieval location for an end user. For example the drop zone may include a chute or the like, a user's hand, or any other area where a dispensable unit is to be released.

As shown in step 414, the method 400 may include releasing the dispensable unit from its engagement with the first end of the tube, e.g., by breaking a bond or connection between the dispensable unit and the retrieval device. In an aspect, the connection between the tube and the dispensable unit is broken by a wall, surface, or other protrusion, that mechanically separates the dispensable unit from the tube as the tube passes over the wall at a predetermined height. The wall may be partially or fully constructed of flexible or soft material, including but not limited to a thermoplastic elastomer (TPE), a thermoplastic rubber (TPR), silicone, and the like in order to avoid damage to the dispensable unit. The wall may further include or work in conjunction with a brush or the like, as this would enable the end of the tube to be brushed clean of any contaminants (such as broken pieces of powders of dispensable unit), which may be advantageous, especially when dispensable units include medical substances such as pharmaceutical products. This "cleaning wall" may additionally include a cleaning substance (including but not limited to ethanol) that can be applied automatically or manually. In another aspect, the wall may provide a cleaning surface for the retrieval device without serving to dislodge a dispensable unit from the retrieval device.

As shown in step 416, the method 400 may include determining a z-axis position where the first end of the tube contacts one or more of the plurality of dispensable units. This information may be useful for a variety of purposes including, e.g., deciding whether to attempt a retrieval and to update a future retrieval pattern according to information about the surface of the dispensable units within the container. In one aspect, the tube may be repositioned at a predetermined height above this z-axis position before additional operations such as attempting a retrieval or moving the tube within the x-y plane.

As shown in step 418, the method 400 may include repositioning the tube to a second position different from the first position within the x-y plane. In an aspect, the second position is offset from the first position within the x-y plane by a distance greater than half of a cross-sectional width of the first end of the tube. The second position may be any position included in a retrieval pattern or retrieval strategy as contemplated herein.

As shown in step 420, the method 400 may include plunging the tube into the container along the z-axis in the second position. It will be understood that the term "plunging" as used herein is intended to represent any general vertical motion (or horizontal motion in a horizontally aligned device), and is not intended to imply any particular force or velocity of motion. In this step 420, the tube may be lowered a predetermined amount from a starting z-axis position, or the tube may be lowered while measuring contact force with the surface of the contents of the container in order to avoid over-insertion or under-insertion into the contents. In one aspect, a low-velocity approach to the surface is preferentially employed in order to avoid damaging the dispensable units.

The steps 402 through 420 may be performed any number of times according to a number of dispensable units that are to be retrieved from a container. This may include a single retrieval or a number or retrievals, or a continuous retrieval of numerous dispensable units until a stopping condition is reached.

As shown in step 422, the method 400 may include rotating a carousel including a plurality of containers for positioning at least one of the plurality of containers relative to the tube. In this manner, the retrieval device may be used with a number of different containers so that a variety of different dispensable units can be controllably dispensed from a system in any desired combination or order. The containers may be arranged radially around the retrieval device in a carousel so that the carousel can be rotated to move one of the containers into an operating region of the retrieval device, or the containers may be arranged linearly or in any other suitable pattern, along with accompanying robotics or the like to move one of the containers into a position where the retrieval device can retrieve dispensable units.

Figure 5:
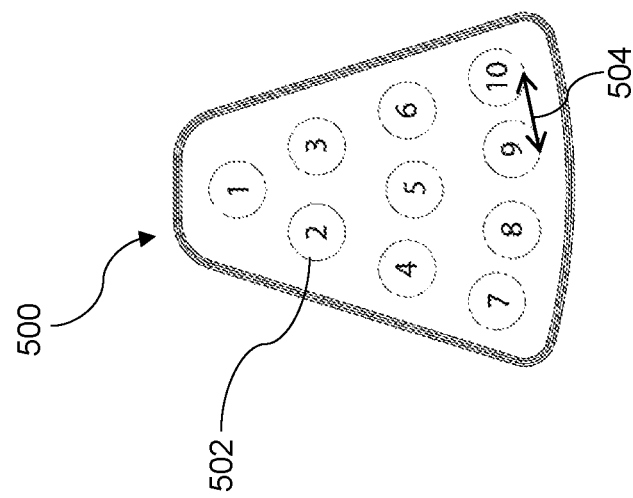
FIG. 5 illustrates a two-dimensional retrieval pattern.

FIG. 5 illustrates a two-dimensional retrieval pattern. In general, the two-dimensional retrieval pattern 500 may represent the plunges taken by a retrieval device into a container for retrieving dispensable units. By way of example, in a vertically aligned system, the retrieval mechanism may be moved horizontally before or after a vertical plunge actuation, iteratively, to follow a retrieval pattern 500 (i.e., a horizontal pattern), thus allowing the vertical plunging of a tube of the retrieval mechanism to occur at different horizontal coordinates 502 within the dispensable unit mixture. A horizontal pattern may involve varying one or both of the horizontal dimensions, or neither. Further, one skilled in the art will recognize that the pattern can be extrapolated to a fully three-dimensional pattern of locations at which plunge actuations could commence. Thus, retrieval patterns discussed herein may also or instead include three-dimensional patterns. Moreover, although this disclosure discusses horizontal two-dimensional retrieval patterns 500 in detail, one of ordinary skill will recognize that this orientation is provided by way of example and convenience only, and other orientations (e.g., vertical two-dimensional retrieval patterns for a horizontal retrieval device configuration) are possible.

The two-dimensional retrieval pattern 500 may be utilized because dispensable unit pickup can have a very low relative success rate if the plunging occurs at the same horizontal coordinates continually, due to a high probability that the vertical plunge will fail to make contact between the first end of the tube and a dispensable unit, thus not allowing for a subsequent strong connection between a dispensable unit and the tube, and instead forcing nearby dispensable units away from the plunging tube. This may create a "hole" or recess in the surface of the dispensable unit mixture, i.e., a location where there are no dispensable units. Subsequent plunges at the same horizontal coordinates may continue to push the tube into this hole or recess, which could make it difficult to connect with and pull out a dispensable unit, as the dispensable unit may be disposed at a lower vertical position than the surface of the dispensable unit mixture, where retrieving it could require overcoming the weight of other dispensable units that are partially or fully above. Retrieval rate may thus be increased by moving the tube in the horizontal plane between vertical actuations, i.e., following a two-dimensional retrieval pattern 500, as this can avoid any such recesses that have been created by unsuccessful plunges, while also advantageously avoiding a need to periodically agitate a container to level the contents, which can damage dispensable units. In an aspect, every iteration of a two-dimensional retrieval pattern 500 (i.e., every horizontal position in a pattern at which a vertical plunge occurs) may be referred to as a step of that two-dimensional retrieval pattern 500.

In an aspect, the horizontal separation 504 between attempted retrievals may be greater than half the width of the average cross-sectional area of the portion of the retrieval device that enters the dispensable unit mixture. This can assure that any previously created recesses will be at least partly avoided in the next plunge. However, a variety of other strategies may be deployed. For example, each retrieval attempt may be a predetermined, minimum distance from a prior retrieval attempt. This may be achieved by following a specific pattern, or by selecting a random direction and moving a distance greater than the predetermined, minimum distance within a horizontal plane. Other strategies may also or instead be employed including strategies that attempt to obtain a largest average move size without repeating retrieval attempt locations, or strategies that work toward or away from the perimeter of the container. More generally, any technique that distributes locations for attempted retrievals throughout a horizontal plane through the container in a manner intended to maximize the success rate of sequential retrieval attempts may be usefully employed in a retrieval strategy as contemplated herein.

In plunging, whether the retrieval device picks up a dispensable unit in a particular plunge or not, the device may contact one or more dispensable units in the mixture, thus exerting a force on the dispensable units and pushing them away from the tube, nib, or other part of the device. As discussed herein, an agitator or the like may be included to increase this displacement. However, given the vertically downward motion of a plunge, a likely scenario is that dispensable units are pushed away from the device in the horizontal direction, which can create holes in the dispensable unit mixture. However, agitation can assist to eliminate holes in the dispensable unit mixture. Thus, agitation of the whole mixture may be useful for increasing the likelihood for successful dispensable unit retrieval, as it randomizes the dispensable units' distribution, orientation, and state within the dispensable unit mixture thus making it less likely that multiple plunges in similar locations to a previously failed plunge will result in repeated failure. Such agitation may also (e.g., due to gravity or some other uniform acceleration, such as centripetal acceleration) eliminate holes or recesses because the dispensable unit mixture level will tend to even out as it is disturbed in such a way (for instance, it may settle substantially "flat"). Thus, implementations may include devices that provide or assist in the agitation. These include, but are not limited to, the agitator discussed herein, the carousel (which may spin, shake, or otherwise move to provide for agitation in a dispensable unit mixture), the tube (e.g., moving along a surface of a dispensable unit mixture in order to agitate the mixture), and so forth. Where dispensable units are fragile, this type of periodic agitation may be avoided or used more sparingly in order to avoid damage to dispensable units.

Figure 6:
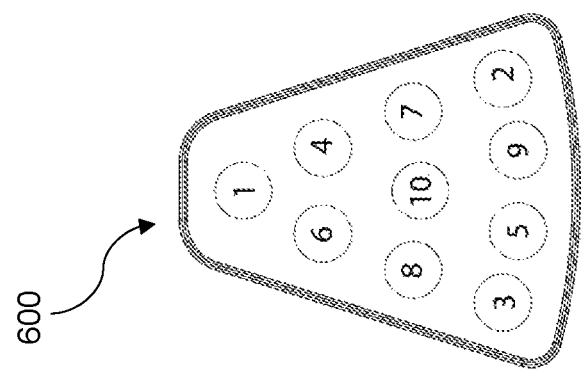
FIG. 6 illustrates a two-dimensional retrieval pattern.

FIG. 6 illustrates a two-dimensional retrieval pattern. In order to continually and most effectively avoid any holes or recesses that are created in the mixture, e.g., by the agitation described herein or otherwise, the two-dimensional retrieval pattern 600 may be such that it covers an entire horizontal area of the dispensable unit mixture at roughly an even spacing. The two-dimensional retrieval pattern 600 may include a winding route or the like to ensure that the minimum distance is traveled by the tube when covering the entire pattern once. The two-dimensional retrieval pattern 600 may also be such that it maximizes the distance between each step of the pattern, which would move the tube as far as possible from the last recess created from a missed plunge. This may increase on average the agitation of the whole dispensable unit mixture at each step, as plunging may be more likely to be unsuccessful in a recess or hole (i.e., an empty space where physical contact with the dispensable units is minimal), and as a result may improve elimination of existing recesses or holes. The two-dimensional retrieval pattern 600 may also be a hybrid of these routing strategies.

Properties of the patterns discussed herein may include without limitation any retrieval height calculated or sensed by the system, or any adjustable property of the device, including but not limited to the speed of plunging and the time between steps or plunges.

Control of the patterns discussed herein, automatic determination of the patterns discussed herein, and multi-axis actuation of the patterns discussed herein, may be performed by, or controlled by, an onboard or offboard microprocessor and associated memory integrated circuits (ICs) (e.g., random-access memory (RAM) chips, erasable programmable read-only memory (EPROM) chips, H-bridge drivers, and the like). Such control systems may allow the mechanism to actuate any number of patterns for different dispensable unit mixtures in proximity to (and in range of) the mechanism, and to remember and continue the progress along each pattern separately.

FIGS. 7-10 show various retrieval system configurations.

As shown in FIG. 7, the system 700 may include the use of a carousel 718 housing a plurality of containers 704 arranged for substantially vertical retrieval of dispensable units contained therein. Each of the containers 704 may include distinct and separate dispensable unit mixtures. The carousel 718 may be arranged substantially in a circle in a horizontal plane. The carousel 718 may rotate as necessary to select different containers 704 and thus different dispensable unit mixtures. In order to prevent contamination, there may be a cover for the containers 704, e.g., that covers all containers 704 except for the container 704 selected for dispensable unit retrieval (i.e., the container 704 that the tube is disposed above). The cover may be movable, e.g., rotatable about the containers 704.

As shown in FIG. 8, the system 800 may include the use of a carousel 818 housing a plurality of containers 804 arranged for substantially horizontal retrieval of dispensable units contained therein. Thus, the carousel 818 may be arranged substantially on its side with respect to gravitational pull. Such an embodiment may allow for loading dispensable unit mixtures from vertically above. As discussed herein, many other configurations are possible.

Figure 9:
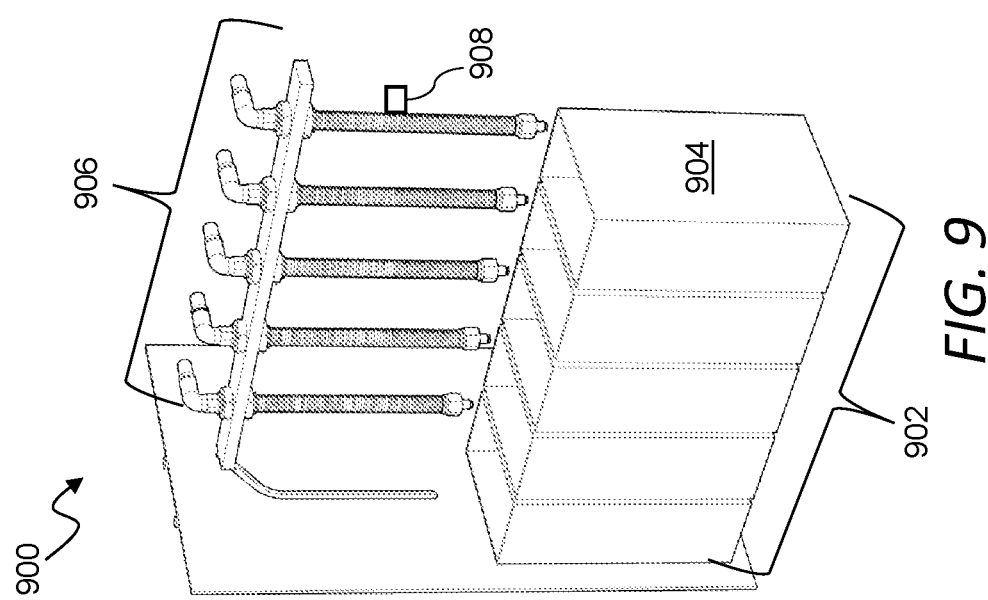

As shown in FIG. 9, the system 900 may include containers 904 arranged in an array 902. In any of the arrangements discussed herein, there may be multiple retrieval mechanisms 906 within the system 900, which can actuate horizontally and vertically either in unison or be controlled independently. In an embodiment including a vacuum pump having a vacuum pressure in the tube, a pressure switching sub-mechanism 908 may be used, which can include, but is not limited to, an array of solenoid valves. The pressure switching sub-mechanism 908 may enable vacuum force to be concentrated in one or more of the tubes, and improve the likelihood of dispensable unit retrieval.

Figure 10:
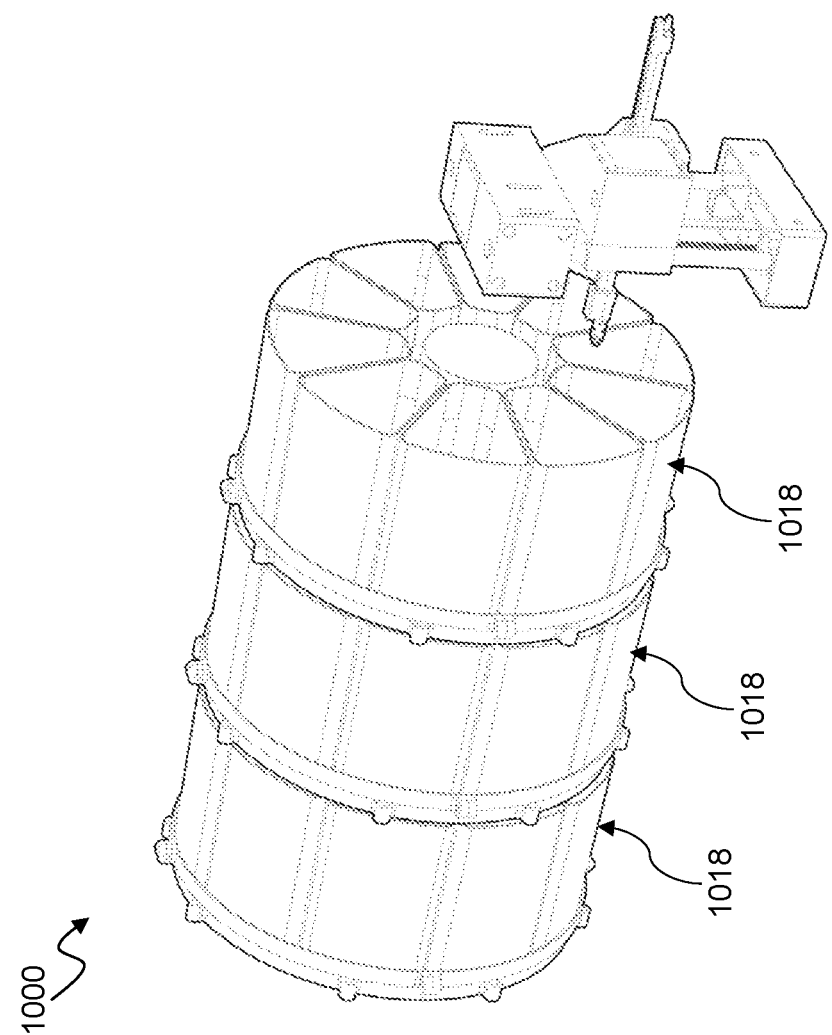

As shown in FIG. 10, the system 1000 may include several carousels 1018 or arrays that stack, e.g., horizontally or vertically. Stacking may occur carousel 1018 by carousel 1018 as in the figure, container by container, or via any other permutation of containers in three-dimensional space, e.g., in a helical or screw arrangement.

In any of the arrangements discussed above, the containers may be removable from the system or device. Additionally, the containers may be attached to the device (e.g., to the carousel) via one of several attachment sub-mechanisms, including but not limited to magnets, electro-magnets, pressure-sensitive tape, mechanical locking (e.g., male-to-female), friction fits, snap fits, and so on.

In implementations, carousel motion may include a high torque or high force actuation. For this reason, human and machine safety may be a concern, for instance if a hand were caught between two containers during carousel motion. For this and other reasons, an electrical failsafe may be implemented where a carousel, which is held within an enclosure and accessible through a door (e.g., for loading), may include a sensor (e.g., an optical-interrupter), that holds a particular voltage (e.g., corresponding to a digital high or digital low) when the door is closed or the whole system or device is safe and secured. The signal to drive the actuation of the carousel may pass from a processor through a gate (before reaching, for instance, a motor driving circuit or chip), where the gate performs a logical 'AND' or 'OR' to enable the actuation only if the sensor value is as expected for a secured (or locked or closed) state.

The containers described herein, e.g., those shown in the figures above, may be arbitrarily sized, shaped, textured and weighted, or may be devised to be of a particular size, shape, texture and weight that is optimized, e.g., for particular dispensable units or for cooperation with particular machinery. In one illustrative container, the material of the container is smooth (i.e., having a low surface friction) to prevent jamming, which can occur in a container made of moderately high surface friction material such as wood or matte plastic. The container may also be relatively lightweight to reduce the power needed to move the container. This material of the container may include without limitation one or more of: polypropylene (e.g., random copolymer or homopolymer), polycarbonate (such as Makrolon), ABS, and the like. The material of the container may also be food-safe, waterproof, or water-resistant by certain regulatory standards such as 21CFR, NSF51, and NSF61. The container may also or instead be made of multiple materials with all or subsets of these properties.

As shown in the figures above, the horizontal planar cross section of an illustrative container may partly or fully be in the shape of a rounded segment to enable a plurality of containers to be arranged in a ring, potentially as part of a rotating carousel as described herein, while omitting sharp edges to prevent jamming or wasted space (e.g., relatively large dispensable units may not be able to fit in corners of the containers having sharp edges). The vertical cross section may be asymmetrical in one of its perpendicular directions, with one or many sections of the container being deeper vertically than other sections. In this manner, due to gravity and sloping container walls, when there is a relatively small number of dispensable units in the container (e.g., if many dispensable units have been retrieved) the dispensable units can gravitate to these deeper sections. Further, the horizontal pattern followed by the mechanisms described herein may spend more time or retrieval steps in these deeper areas of the container, as there could be a much greater chance of finding dispensable units in these areas. The devices may also or instead utilize a known axial location of a surface of the dispensable unit mixture for concentrating in these areas. For instance, if the axial position of the surface is relatively low in the container, then the device may know to focus in the deeper areas of the container, thereby adjusting its horizontal two-dimensional pattern to concentrate in a smaller section in these areas (e.g., shrinking the pattern).

The container may also or instead include features that allow for easy extraction and loading into the mechanisms described herein, e.g., the carousel. These features may include without limitation holes, grooves, handles, magnets, and so forth. These features may be disposed below a sloping floor of the container, to ensure that internal volume of the container is not affected. The containers may also or instead include features that enable a secure docking, attachment, or locking to corresponding features on a carousel or another device. A carousel or another device for engaging with the containers may also or instead include protrusions or the like to force improperly or insecurely attached containers into a correct, secure position. These protrusions may secure the container when the carousel rotates, thereby imposing a radial inward force from a fixed or rotating portion of the carousel onto the offending container, e.g., driving it in place.

The container may have surfaces for use in cleaning the retrieval mechanism, particularly, though not limited to, the nib, which can accumulate a build-up of contaminants or residue over time. For example, the nib may compress upon being forced towards the cleaning surface, thus exerting a force on any built up contaminants. The cleaning surface may include a horizontal lip or the like present on one or several edges or sides of the container. The cleaning surface may also be slightly angled from a horizontal plane such that any contaminants that are dislodged fall into the container from which they originated. While making contact with the cleaning surface, the mechanism may further move in a horizontal direction to perform a wipe that can remove other residue or contaminants.

A container may function as a chute for receiving retrieved dispensable units. A reason for such a container/chute can include instances where there is only one degree of horizontal motion, thereby necessitating that the horizontal dimension used for changing pattern locations horizontally is the same as the dimension used to move the mechanism above the chute for dropping retrieved dispensable units. In this case, other containers may also have a design that enables such a one dimensional horizontal pattern, for instance, a bottom that is contoured to be vertically sloped not only in the radial direction but also the tangential direction with respect to a rotating carousel.

The container may have a globally unique or categorizing identifier upon it, such as one or more of a barcode, a quick response (QR) code, a near field communication (NFC) tag, or a radio-frequency identification RFID tag. This may allow the retrieval mechanism, in conjunction with a reading or scanning component, to identify a container including any unique properties for the container and the dispensable unit mixture contained therein (e.g., average dispensable unit size, total dispensable unit count, and so on). Such a feature may form part of an e-commerce system where empty or near-empty containers trigger (e.g., using the depth information described herein) an automatic re-ordering of more containers that coincide with the near-empty identified container or more dispensable units.

The container may have a resealable opening (e.g., a living hinge or an adhesive top). This may form part of an e-commerce system where partial containers may be sealed and removed, and where financial payments may be made based on how much of the dispensable unit mixture was dispensed during a particular time period.

The mechanisms described herein and associated containers may contain or be disposed adjacent to storage chambers for dispensable units or non-unit materials or mixtures that are not supported for dispensing by specific mechanisms or specific containers. This may allow for a more holistic operation of the mechanisms, for instance a pill dispenser that operates only on pills, but is adjacent to other medical supplies like bandages given the possible overlapping use cases (e.g., in a first aid cabinet).

Dispensable Unit Identification

Figure 11:
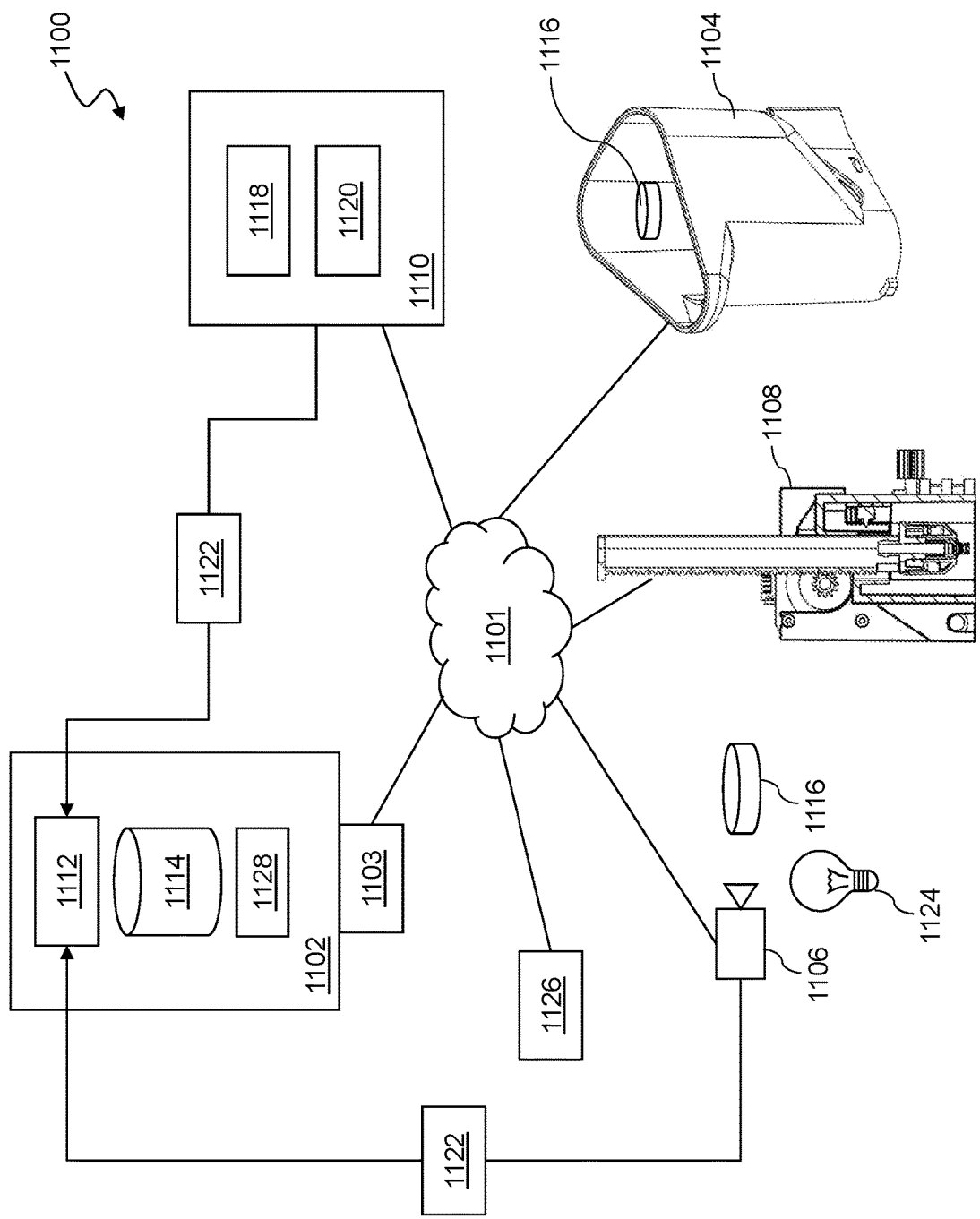
FIG. 11 illustrates a system for dispensable unit identification.

FIG. 11 illustrates a system for dispensable unit identification. In general, the system 1100 may include components and participants for detecting a dispensable unit's properties. For example, the system 1100 may be used for the detection or identification of one or more of the following: a count of dispensable units (e.g., the number of dispensable units physically within a known location or container), which may be used to relay back to a user the state of a container (i.e., whether it is full or empty); and a shape, size, weight, and texture/surface friction of the dispensable units. The properties of the dispensable units may be used for any dispensing process, e.g., a vacuum assisted process (i.e., a pick-and-place mechanism), a gravity assisted mechanism that utilizes a chute (e.g., where the chute size is electronically controlled based on dispensable unit size), and so forth. The dispensable unit's properties detected and identified by the dispensable unit identification systems described herein may be utilized in the formation of a retrieval pattern as described herein, or steps included in the retrieval pattern.

The system 1100 may include a computing device 1102, a container 1104, an optical sensor 1106, a retrieval robot 1108, and a measurement device 1110. The aforementioned participants and components of the system 110 may be in a communicating relationship with one another, e.g., through a data network 1101.

The data network 1101 may be any network(s) or internetwork(s) suitable for communicating data and control information among participants in the system 1100. This may include public networks such as the Internet, private networks, telecommunications networks such as the Public Switched Telephone Network or cellular networks using third generation (e.g., 3G or IMT-2000), fourth generation (e.g., LTE (E-UTRA) or WiMax-Advanced (IEEE 802.16m)) and/or other technologies, as well as any of a variety of corporate area or local area networks and other switches, routers, hubs, gateways, and the like that might be used to carry data among participants in the system 1100. The data network 1101 may include wired or wireless networks, or any combination thereof. One skilled in the art will also recognize that the participants shown the system 1100 need not be connected by a data network 1101, and thus can be configured to work in conjunction with other participants independent of the data network 1101.

Communications over the data network 1101 may be made possible through one or more communications interfaces 1103 present on one or more of the components of the system 1100. The communications interface 1103 may include, or be connected in a communicating relationship with, a network interface or the like. The communications interface 1103 may include any combination of hardware and software suitable for coupling the components of the system 1100 to a remote device (e.g., the computing device 1102) in a communicating relationship through the data network 1101. By way of example and not limitation, this may include electronics for a wired or wireless Ethernet connection operating according to the IEEE 802.11 standard (or any variation thereof), or any other short or long range wireless networking components or the like. This may include hardware for short range data communications such as Bluetooth or an infrared transceiver, which may be used to couple into a local area network or the like that is in turn coupled to a data network such as the Internet. This may also or instead include hardware/software for a WiMax connection or a cellular network connection (using, e.g., CDMA, GSM, LTE, or any other suitable protocol or combination of protocols).

The computing device 1102 may include a processor 1112 and a memory 1114. The computing device 1102 may include any devices within the system 1100 operated by users to manage, monitor, communicate with, or otherwise interact with other participants in the system 1100. This may include devices (e.g., remote devices) such as desktop computers, laptop computers, network computers, tablets, smart phones, smart watches, PDAs, or any other devices that can participate in the system 1100 as contemplated herein. In one aspect, the computing device 1102 (and a user interface thereof) is integral with another component in the system 1100.

The computing device 1102 may generally provide a user interface 1128, which may include a graphical user interface, a text or command line interface, a voice-controlled interface, and/or a gesture-based interface. In general, the user interface 1128 may create a suitable display on the computing device 1102 for user interaction. In implementations, the user interface 1102 may control operation of one or more of the components of the system 1100, as well as provide access to and communication with resources of the system 1100.

The user interface 1128 may be maintained by a locally executing application on the computing device 1102 that receives data from one or more of the components of the system 1100 or other resources. In other embodiments, the user interface 1128 may be remotely served and presented on one of the computing devices 1102. In implementations, the user interface 1128 may also or instead be provided by and/or disposed on another participant in the system 1100.

The container 1104 may be any as described herein, and may for instance be shaped and sized to hold a plurality of dispensable units 1116.

The optical sensor 1106 may be configured to detect an optical property of one of the plurality of dispensable units 1116 prior to placement in the container 1104. The optical sensor 1106 may include one or more of the following: a CMOS device, a CCD device, an opto-interrupter, a reflective object sensor, and the like. The optical sensor 1106 may be disposed within another participant in the system 1100, or it may be a standalone participant within the system 1100. In an aspect, the optical sensor 1106 is disposed in the container 1104. In another aspect, the optical sensor 1106 may be separate from the container 1104, and used independently to analyze dispensable units 1116, e.g., before they are place into the container 1104 for distribution by the retrieval robot 1108. In this manner, retrieval operations may be usefully optimized to a particular dispensable unit without a need for the local container 1104 or retrieval robot 1108 to perform any measurements. Instead, information about the properties can be stored and transmitted to the retrieval robot 1108 for use in generating retrieval strategies for the dispensable units, and this information may be recovered using, e.g., an identifier for the dispensable units or information provided by a user about the dispensable units.

The optical property detected by the optical sensor 1106 may include without limitation one or more of a texture of the dispensable unit 1116, a shape of the dispensable unit 1116, and a size of the dispensable unit 1116, and so on. This information may help to characterize how the items will pack, settle, and move relative to one another, which may be useful in determining, e.g., how best to create and execute a retrieval strategy, and how much contact force might be required to successfully execute the retrieval of a single item. In one aspect, the optical sensor 1106 is configured to detect the optical property using light obstruction, where the optical property includes at least one of a size and shape of the dispensable unit 1116. For example, the optical sensor 1106 may detect an amount of light being obstructed from a known array of light, where this value can be used to determine the size of the dispensable unit 1116. In another aspect, the optical sensor 1106 may be a camera or the like that captures an image of one of the dispensable units 116 for analysis. In implementations, the optical sensor 1106 may be configured to provide a signal 1122 indicative of the optical property to another component, e.g., the processor 1112 of the computing device 1102. Any number of light sources may be used in combination with the optical sensor 1106 in order to detect or identify properties of one of the dispensable units 1116.

The retrieval robot 1108 may be any as described herein, and may for instance be configured to retrieve objects from within the container 1104, e.g., the dispensable units 1116.

The measurement device 1110 may include a strain gauge 1118 and circuitry 1120 configured to provide a signal 1122 indicative of a detected weight of one or more of the container 1104 and a dispensable unit 1116. For example, in an aspect, the measurement device 1110 provides a detected weight of one or more of the plurality of dispensable units 1116 prior to placement in the container 1104. In an aspect, the detected weight of the container 1104 yields the weight of the dispensable units 1116 within the container when the weight of the empty container 1104 is known. In another aspect, when the weight of the empty container 1104 and the weight of an individual dispensable unit 1116 (or the weight of a certain amount of dispensable units 1116) is known, the detected weight of the container 1104 yields the amount of the dispensable units 1116 within the container 1104. A suitably sensitive measuring device 1110 may also provide additional information, such as when a single dispensable is removed, how much contact force a retrieval device is applying to the container, and how many items are left in the container. This information can facilitate a blind retrieval task as contemplated herein by providing non-optical feedback useful in planning and executing a retrieval strategy.

The measurement device 1110 may also or instead include one or more cantilevers for supporting the container 1104, e.g., a platform of similar size to the containers 1104. The cantilever may be attached such that a force (e.g., including, but not limited to, weight) on the cantilever causes a deformation. On such a measurement device 1110, a user may activate a "measurement mode" or the like, or it may be activated automatically. Upon activation of a measurement mode, the measurement device 1110 may measure the weight of a container 1104 (empty or otherwise) and store that data in a memory 1114. In an aspect, the weight of an empty container 1104 and the known weight of a dispensable unit 1116 may be used to calculate an amount of dispensable units 1116 present in the container 1104 at a given time.

The processor 1112 may be configured to receive the signal 1122 and to use the detected weight and the optical property to execute a blind dispensing operation of one of the plurality of dispensable units 1116 from the container 1104 using the retrieval robot 1108. In one aspect, the processor 1112 is part of a controller or the like (e.g., as described above), or the processor 1112 is in communication with the controller, for controlling operation of the retrieval robot 1108. For example, the processor 1112 may be configured to adjust a speed of the blind dispensing operation based on at least one of the detected weight and the optical property. In an aspect, when the detected weight is over a predetermined weight (e.g., indicating that the container 1104 includes relatively heavy dispensable units 1116), the processor 1112 is configured to set the speed of the blind dispensing operation below a predetermined speed. In other words, in an aspect, the weight of the dispensable unit is a factor used to determine the speed of the retrieval robot 1108, where the heavier the dispensable unit, the slower the movement of the retrieval robot 1108. Other properties of the dispensable unit may also or instead be used to configure aspects of the settings or operation of the retrieval robot 1108.

In an implementation, the optical sensor 1106 is configured to detect an optical property of a portion or group of the plurality of dispensable units 1116, and the processor 1112 is configured to determine whether the portion of the plurality of dispensable units 1116 includes dispensable units 1116 of different types based on the optical property of the portion. In this manner, the system 1100 can identify whether the plurality of dispensable units 1116 includes a mixture of different types of units, or if the plurality of dispensable units 1116 are of the same type of units. The specific type or types of dispensable units 1116 may also or instead be detected and identified using the system 1100.

The system 1100 may further include a light source 1124. The light source 1124 may be configured to produce a light having a plurality of different frequencies for cooperation with the optical sensor 1106 in detecting a texture of one or more of the dispensable units 1116. To this end, the optical sensor 1106 may be configured to detect the texture of the dispensable unit 1116 by measuring diffusion, dispersion, and strength of the light returned to the optical sensor 1106 when light from the light source 1124 is illuminated onto the dispensable unit 1116.

The system 1100 may further include other devices 1126 including without limitation one or more of a camera, an acoustic sensor, a capacitive sensor (e.g., capacitive touch sensors and capacitive distance sensors), and an inductive sensor. The other devices 1126 may also or instead include input devices including a keyboard, touchpad, mouse, switches, dials, buttons, sensors, and the like, as well as output devices such as a display, a speaker or other audio transducer, light emitting diodes, and the like. Other devices 1126 may also or instead include a variety of cable connections and/or hardware adapters for connecting to, e.g., external computers, external hardware, external instrumentation or data acquisition systems, and the like.

The system 1100 described above, or one of its components or participants, may communicate with a user, e.g., through a network interface or the like. For example, the system 1100 may query the user to verify information, e.g., a number of dispensable units 1116 added to a container 1104, or to verify a specific property detected by the system 1100. This communication may be accomplished through one or more of the following: text message, push notification, a device's onboard display, a voice or sound communication, a vibration or other alert, a touch of buttons or a touch screen, and the like.

Figure 12:
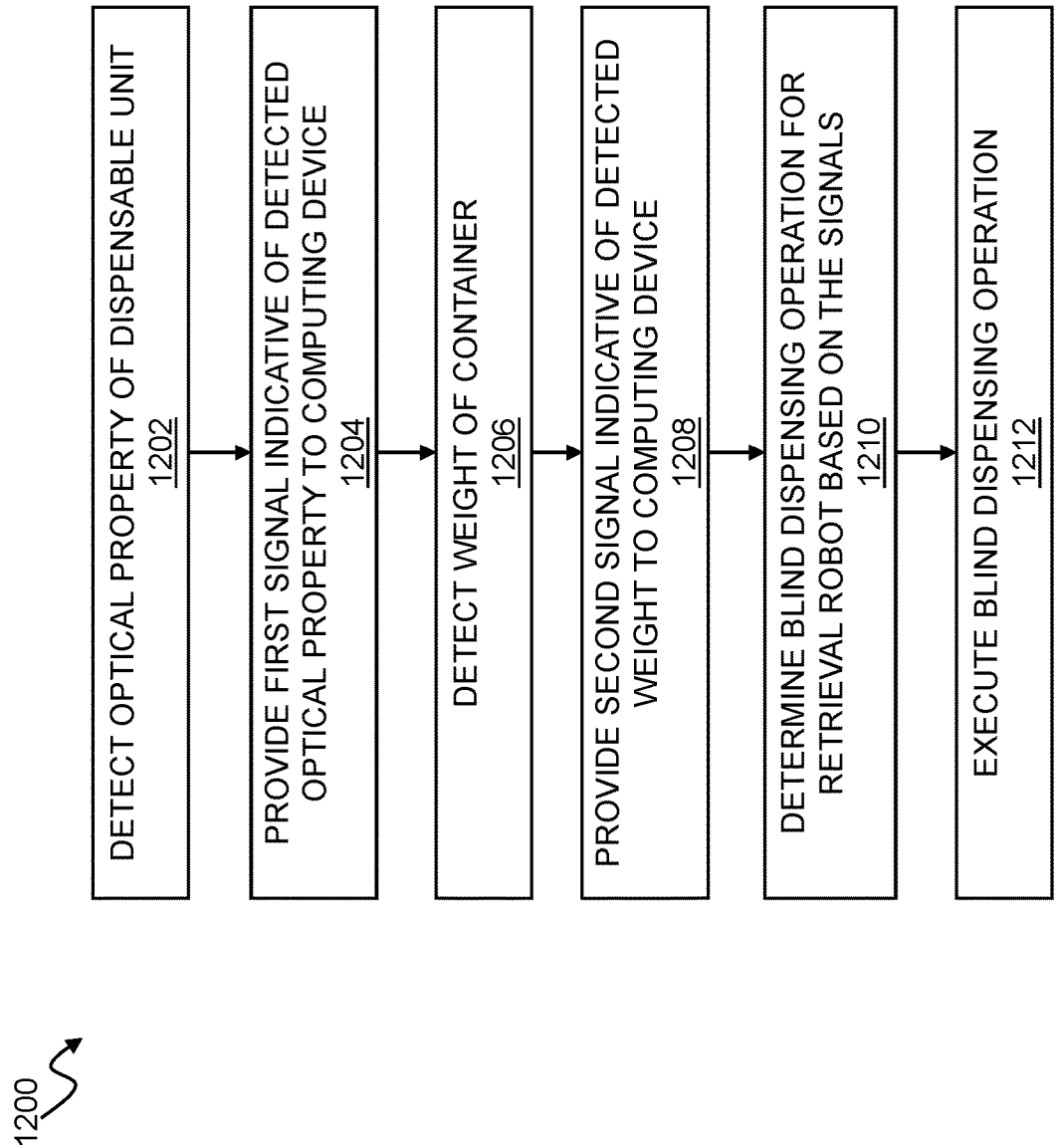
FIG. 12 is a flow chart of a method for dispensable unit identification.

FIG. 12 is a flow chart of a method for dispensable unit identification.

As shown in step 1202, the method 1200 may include detecting an optical property of a dispensable unit. This may usefully be performed prior to placement of the dispensable unit in a container that is shaped and sized to hold a plurality of dispensable units for distribution using a device as contemplated herein. An optical sensor or the like may be used to detect the optical property of the dispensable unit.

Detecting an optical property of a dispensable unit may include illuminating the dispensable unit with a light source that produces a light having a plurality of frequencies; measuring diffusion, dispersion, and strength of light returned to an optical sensor; and detecting a texture of the dispensable unit from the measured diffusion, dispersion, and strength.

Detecting an optical property of a dispensable unit may also or instead include using light obstruction, e.g., for detecting at least one of a size and shape of the dispensable unit. For example, the device may determine the size of the dispensable unit based on how much light is obstructed from an array of LEDs shining at the dispensable unit. The LEDs may also or instead send an amplitude or frequency modulated signal, whose receipt may be Fast Fourier Transformed (FFT) by the sensors to determine the amount of light obstruction. Detecting an optical property of a dispensable unit may also or instead include machine vision, i.e., edge detection of dispensable unit's edges in a two-dimensional image, or use of side-lighting to detect surface features or textures.

The method 1200 may also include detecting an optical property of numerous dispensable units in a group, and determining whether this group of dispensable units includes dispensable units of different types based on the optical properties of the group and individual items in the group.

As shown in step 1204, the method 1200 may include providing a first signal to a computing device including a processor and a memory, the first signal indicative of the detected optical property.

As shown in step 1206, the method 1200 may include detecting a weight of one or more of the container and a dispensable unit using a measurement device.

As shown in step 1208, the method 1200 may include providing a second signal to the computing device, the second signal indicative of the detected weight of the container.

As shown in step 1210, the method 1200 may include determining a blind dispensing operation for retrieving one of the plurality of dispensable units from the container with a retrieval robot using information included in at least one of the first signal and the second signal. The blind dispensing operation may include executing a retrieval pattern as discussed herein. Thus, determining the blind dispensing operation may include determining the use of a specific retrieval pattern, determining steps for a retrieval pattern, formulating a retrieval pattern from scratch, adjusting a retrieval pattern, and so forth. Determining the blind dispensing operation may also or instead include determining other parameters for retrieval include speed, acceleration, trajectories, drop zones, cleaning schedules or procedures, and so forth.

As discussed generally herein, optical and weight information may be used in a variety of ways. For example, the weight may be used to determine how many units are in a container or when the container might be empty. Weight may also be used to quickly check for a successful retrieval attempt, or to measure the force that a retrieval device is applying to items in a container. The optical properties may be used, e.g., to estimate a contact force and/or vacuum force required to securely bind a dispensable unit with a vacuum-based retrieval nib. In another aspect, the optical properties may be used to estimate size or weight of individual units, so that a sufficient vacuum force can be applied, and so that retrieval attempts (e.g., included in a sequence) are spaced a suitable distance apart. More generally, any use of weight and optical properties as contemplated herein may be used to augment and improve a blind retrieval process and eliminate or mitigate the need for machine vision or similar image analysis as an aid to navigation during retrieval.

As shown in step 1210, the method 1200 may include executing the blind dispensing operation. In particular, it is contemplated that a dispensing operation including, e.g., retrieval and distribution, can be performed (or at least attempted) without any supporting visual information. This can advantageously simplify the hardware required to successfully distribute dispensable items from a container and eliminate the need for cameras, illumination, and supporting communication circuitry within the system.

The method 1200 may also or instead include performing error checks. An error check may include determining whether the weight of the dispensable units that was measured is a multiple of the weight of an originally measured dispensable unit (within a certain margin of error). Another error check may use one or more cameras disposed within a container for viewing the dispensable units from a variety of angles to ensure that the visible added dispensable units have the same or similar properties, and to ensure that no residue or other contaminant is present in the container. This may be coupled with a vibration actuation (e.g., via a motor or the like) of the container to agitate the dispensable units, e.g., for exposing more dispensable units for the line of sight of the camera for verification. Notifications to a user (or another component or participant in the system) may be sent based on the outcome of the error checks.

Networked Notification for Dispensable Units

Figure 13:
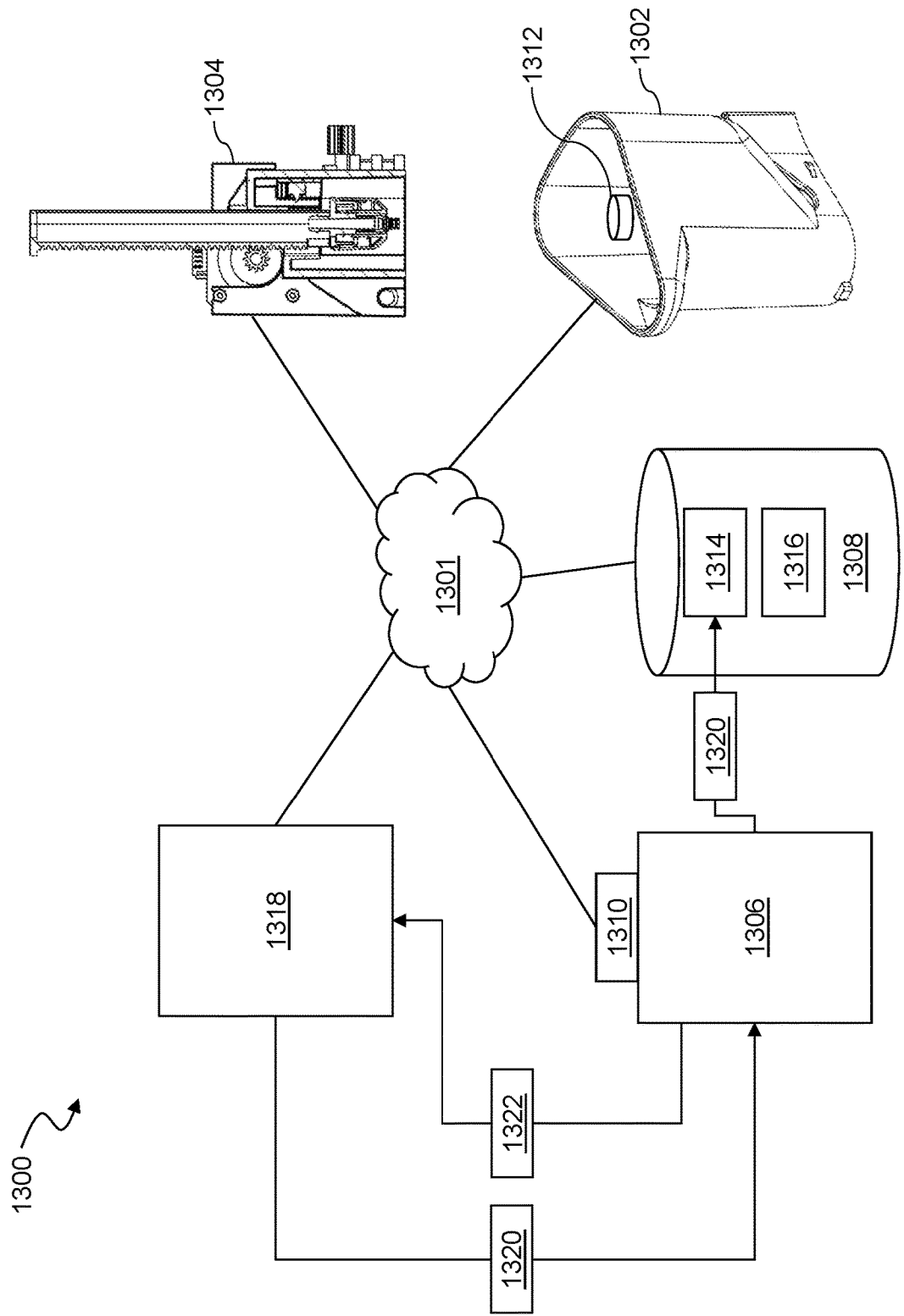
FIG. 13 illustrates a system for networked notification for dispensable units.

FIG. 13 illustrates a system for networked notification for dispensable units. The system 1300 may be useful, e.g., for controlling distribution of sensitive dispensable units. The system 1300 may also or instead be utilized with any of the aforementioned devices, systems, and methods, including without limitation any of the retrieval mechanisms and containers discussed above.

The system 1300 may include a container 1302, a dispensing system 1304, a processor 1306 and a memory 1308, and one or more network interfaces 1310 to couple components of the system 1300 to a data network 1301.

The container 1302 may be any as described herein. For example, the container 1302 may be configured to hold a plurality of dispensable units 1312 subject to managed distribution according to a number of rules 1314 and/or a predetermined schedule 1316. For sensitive dispensable units, the container 1302 may be fortified in a number of ways. In one aspect, tamper-proof mechanisms may be installed in order to prevent access to contents without use of the corresponding dispensing system 1304. While it may be difficult to physically secure such a container 1302 against all entry attempts, a certain degree of physical strength to the container 1302 may discourage more casual efforts at unauthorized entry. And it is relatively straightforward to detect tampering and entry in a manner that can be immediately reported when the tampered-with device is coupled to or communicating with the dispensing system 1304. This information may be usefully communicated to appropriate authorities or other personnel for further action. Thus, more generally the container may be tamper proof, and may be configured to report tampering events when possible. In addition, the dispensing system 1304 may be configured to prohibit further distribution from the container 1302 after a tampering event is detected. This may be useful in a variety of contexts contemplated herein, including contexts where controlled substances or the like are distributed in containers, or contexts where a pharmaceutical in a container is recalled globally, expires, or is contraindicated for a particular patient.

The dispensing system 1304 may be any as described herein. For example, the dispensing system 1304 may be operable to dispense the plurality of dispensable units 1312 from the container 1302.

The processor 1306 and the memory 1308 may be operatively connected to the container 1302 and the dispensing system 1304. The processor 1306 and the memory 1308 may be disposed on, or in communication with, a computing device such as any as described herein.

The processor 1306 may be configured to dispense one or more of the plurality of dispensable units 1312 according to at least one of the predetermined schedule 1316 and the number of rules 1314.

The memory 1308 may store the predetermined schedule 1316 and the number of rules 1314, or the predetermined schedule 1316 and the number of rules 1314 may otherwise be accessible to the processor 1306, e.g., through the data network 1301.

The network interface 1310 may couple one or more of the participants in the system 1300 to the data network 1301. For example, the network interface 1310 may couple one or more of the processor 1306, the memory 1308, and a remote resource 1318 to the data network 1301. Additionally, other components of the system 1300 may also or instead include network interfaces 1310 for coupling to the data network 1301.

The plurality of dispensable units 1312 may be any as described herein. In an aspect, the plurality of dispensable units 1312 may include at least one controlled substance. The controlled substance may have particular rules included in the number of rules 1314 related to its distribution and use. The controlled substance may also or instead be subject to particular predetermined schedules 1314 for its distribution and use.

The rules 1314 may include a tracking rule related to at least one of a dosage conflict, an illegal use, and a high-risk use of one or more of the plurality of dispensable units 1312. The tracking rule may be checked for accuracy on a predetermined basis, e.g., automatically or by a user of the system 1300. The tracking rule may be specifically tailored to a particular dispensable unit included in the plurality of dispensable units 1312.

The rules 1314 may also or instead include instructions provided for, or regulations related to, the distribution and use of one or more of the plurality of dispensable units 1312. The rules 1314 may be stored in a database, e.g., in the memory 1308 or on the remote resource 1318. The rules 1314 may be subject to random or scheduled updates.

The rules 1314 may be provided by a regulatory agency, a corporation, a manufacturer, a physician or other prescribing party, a third party, a family member, a user, an administrator, a hospital, an insurance company, a pharmacy, and so forth.

The predetermined schedule 1316 may include any time-based or event-based regime related to the dispensable units 1312, e.g., when they should be dispensed or consumed, how long they remain effective (e.g., an expiration date), a recall schedule, and so forth. The predetermined schedule 1316 may be stored in a database, e.g., in the memory 1308 or on the remote resource 1318. The predetermined schedule 1316 may be subject to random or scheduled updates. The predetermined schedule 1316 may be provided by a regulatory agency, a corporation, a manufacturer, a physician or other prescribing party, a third party, a family member, a user, an administrator, a hospital, an insurance company, a pharmacy, and so forth.

The remote resource 1318 may include without limitation one or more of a physician's office, a law enforcement agency, a mobile device, a regulatory body, a government agency, a corporate database, a manufacturer of one of the plurality of dispensable units 1312, and so forth. The remote resource 1318 may also or instead include a user device, e.g., a smart phone, a tablet, a computer, and so forth. The remote resource 1318 may also or instead include a publicly or privately available source of rules and schedules, e.g., on a webpage hosted by a server or the like. In another aspect, the remote resource 1318 is another component of the system 1300 such as the container 1302 or the dispensing system 1304. In general, the remote resource 1318 may be capable of providing updates to one or more of the predetermined schedule 1316 and the number of rules 1314.

In an aspect, the processor 1306 is configured to receive an update 1320 to the predetermined schedule 1316 or the number of rules 1314 from the remote resource 1318 through the data network 1301. The update may include, e.g., a recall of the plurality of dispensable units 1312, a change in the predetermined schedule 1316 or the number of rules 1314, and so forth. The update may also or instead include an interpretation of the predetermined schedule 1316 or the number of rules 1314, or an application/instruction related to the predetermined schedule 1316 or the number of rules 1314.

In another aspect, the processor 1306 may also or instead be configured to transmit a notification 1322 based on a detected event at one or more of the container 1302 and the dispensing system 1304. The update 1320 may thus be received in response to the detected event.

The update 1320 may include an update to a tracking rule as described herein. The update 1320 may also or instead include a verification of the tracking rule, a particular configuration of the tracking rule, a confirmation of the tracking rule, and an execution of the tracking rule. The update 1320 may instead include an alert regarding the tracking rule—e.g., an alert to a user to configure, confirm, execute, or otherwise perform an action/verification related to the tracking rule.

The detected event may include without limitation one or more of the following: a dispensing of one or more of the plurality of dispensable units 1312; that a dispensable unit 1312 has not been dispensed at a predetermined time; a detected environmental condition; that an amount of dispensable units 1312 in the container 1302 has fallen below a predetermined threshold amount; and the like. The notification 1322 may be directly related to the detected event. For example, where the amount of dispensable units 1312 in the container 1302 has fallen below a predetermined threshold amount, the notification 1322 may include sending a request to receive additional dispensable units 1312.

The notification 1322 may be transmitted to one or more of the following: a treating physician for a user of the plurality of dispensable units 1312; a manufacturer of one of the plurality of dispensable units 1312; a pharmacy for a user of the plurality of dispensable units 1312; an insurer of a user of the plurality of dispensable units 1312; and the like.

In another aspect, the processor 1306 is configured to transmit a notification 1322 of a potential misuse (or otherwise event of interest) related to the plurality of dispensable units 1312 to the remote resource 1318 through the data network 1301. The potential misuse may include without limitation one or more of a misdosage, a dispensing of a dispensable unit 1312 by an unauthorized user, that a dispensable unit 1312 has not been dispensed at a predetermined time, and at least one of a certain range of dispensable units 1312 being dispensed in a predetermined time period and a certain combination of dispensable units 1312 being dispensed in a predetermined time period. The potential misuse may also or instead include the violation of a rule, e.g., a tracking rule as described herein, or a deviation from the predetermined schedule 1316.

In general, the above system 1300 may be useful for sending notifications 1322, and it may be used with any of the other devices, systems, and methods described herein. For example, notifications 1322 may relate to the dispensation of dispensable units 1312, or more narrowly consumable items. By way of example, such notifications 1322 may include alerts related to a missed medicine dose or the like. By way of further example, the notifications 1322 may also or instead include direct notifications/messages sent to emergency services if certain dispensable units 1312 are not dispensed or consumed within a certain timeframe.

The notifications 1322 may include any as described herein or otherwise known in the art including without limitation text message, e-mail, phone calls, video, push notifications, vibrating alerts, visual alarms or alerts, and so forth.

Figure 14:
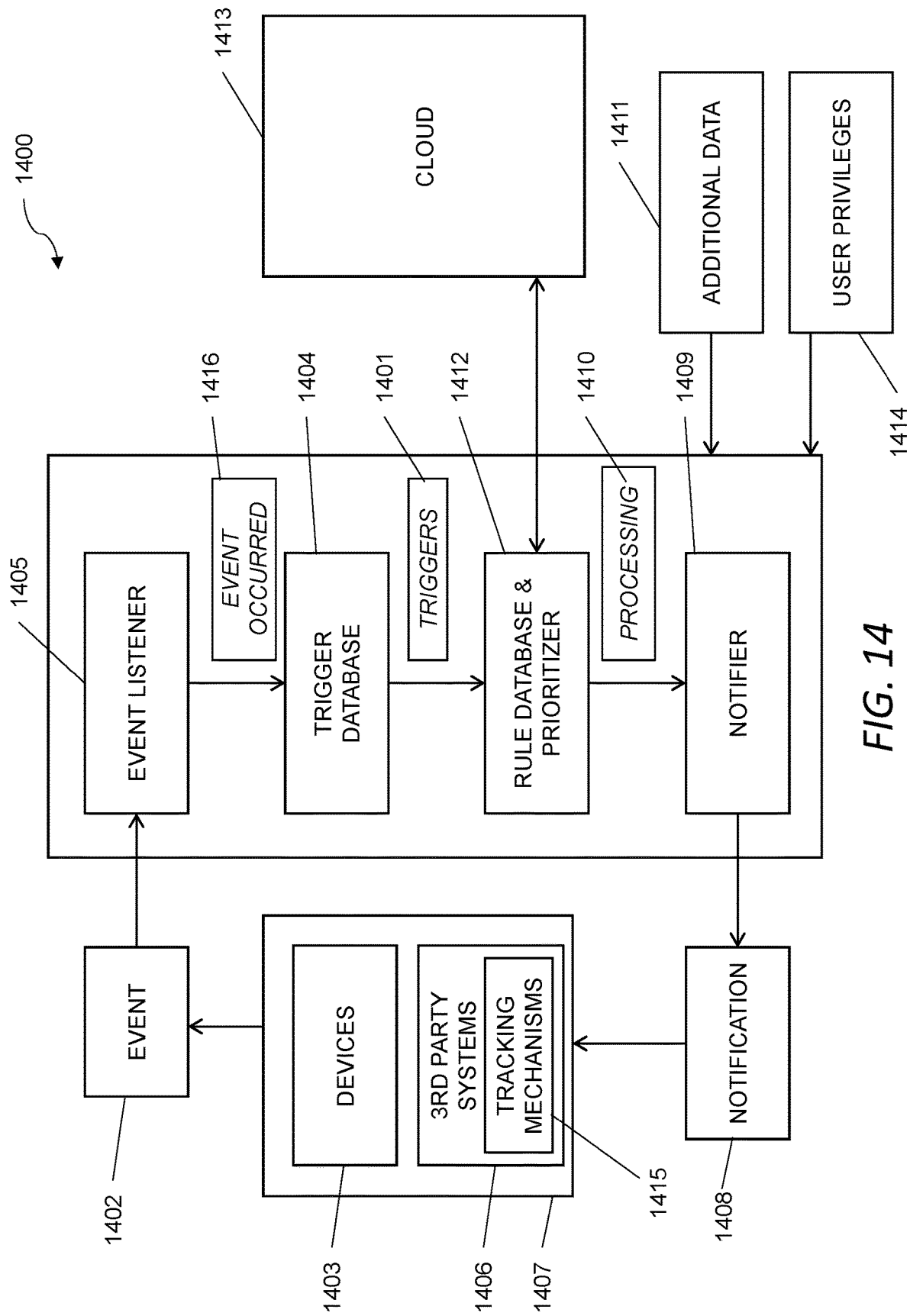
FIG. 14 illustrates another system for networked notification for dispensable units.

FIG. 14 illustrates another system for networked notification for dispensable units.

The system 1400 may have a set of static or dynamic triggers 1401 corresponding to one or more observed events 1402, e.g., external events. If the system 1400 is coupled with a device 1403, e.g., a connected device that manages and/or dispenses dispensable units, illustrative events 1402 may include, without limitation, that a dispensable unit is dispensed or that a scheduled dispensable is not dispensed on time, and illustrative triggers 1401 may include, without limitation, that too few dispensable units were dispensed in a particular time period, or too many, or an incorrect or unsafe combination of dispensable units. The system 1400 may query a trigger database 1404 to ascertain if events 1402 observed by the system 1400 correspond to static triggers 1401, or if a set of environmentally dependent triggers have been achieved. Events 1402 may be looked up, stored, or processed in connection with the trigger database 1404, having been detected via one or more event listeners 1405. The event listeners 1405 may detect that the event has occurred 1416.

Other example events 1402 may include, without limitation, that a particular sensor records a particular temperature or records a particular humidity (or other environmental condition). Corresponding example triggers may include, without limitation, that the temperature of the recorded environment is too high, or the recorded humidity is too humid, or is otherwise outside some predetermined criteria.

The system 1400 may have a set of connected devices 1403 and third party systems 1406, which may be collectively referred to as "external services" 1407. External services 1407 may include but are not limited to smartphones, cellphones, tablets, desktops, laptops, projector systems, digital billboards, advertising systems, quantified-self devices, other personal health devices and accessories, medical databases, home/enterprise security services, smart-home systems, home appliances ground/air transportation/fulfillment services, drone services/platforms, and the like.

External services 1407 may function as inputs to the system 1400, where an event 1402 that occurs at that external service 1407 activates a trigger 1401 in the system 1400, based on the static and dynamic triggers associated with the system, which may be disposed in a trigger database 1404. For instance, a fall detector connected to the system 1400, upon detecting the fall of an elderly patient who is using the same, may communicate with the system 1400 that such an event 1402 has occurred.

External services 1407 may also function as outputs of the system 1400, where the system 1400 sends a notification 1408 (e.g., including certain content) via a notifier 1409 (e.g., including, but not limited to, a wireless antenna and a data bus) with a particular content to one of the external services 1407 in a determined format based on upon its processing 1410 of inputs (and triggers). The processing 1410 may include selecting a rule to handle the trigger 1401. The content of each notification 1408 may be determined based on some additional data 1411, including, but not limited to, news/media data, other authored content, user data (for instance medical data and historical usage data), user privileges, pre-determined external-service-specific content templates, and the like. Content may be human-readable or machine instructions. For instance, upon detecting that a user's medicine supply is low, the system 1400 may send a notification 1408 in the form of an instruction to an e-commerce server to place an order to purchase more. For further instance, upon detecting a patient has had an accident while walking outside, the system 1400 may send a notification 1408 in the form of an instruction 1408 to a medical drone service to dispatch immediate medical help.

The system 1400 may perform processing of its input data (e.g., the external event 1402) to determine which outputs to activate (e.g., notifications 1408) and with what content. Such processing includes but is not limited to usage and goal analytics, risk assessment (e.g. for medical contamination or adverse pill mixing or upon recall of a particular drug), and data aggregation and statistical functions.

There may be a cascading or escalating chain of notification inputs (e.g., triggers/events 1401/1402), which the system 1400 may use to prioritize input events 1402 while determining what action to take for a particular trigger 1401, in a rules database and prioritizer 1412 (e.g., a prioritization function). For instance, the system 1400 may prioritize events 1402 or resulting triggers 1401 from a direct text message by a doctor or from an electronic fall detector over events/triggers from a pedometer. Such cascading may be set up in advance or may be dynamically determined, for instance according to reliability and use cases of the particular external service 1407.

There may be a cascading or escalating chain of notification outputs. For instance, illustratively, notifications 1408 may first be sent to a vibrating wristband on a patient, second as a text message to a cellphone, third as an automated phone call to a patient's doctor, fourth to the emergency services near the patient.

The cascading or escalating chain of notification inputs (e.g., triggers/events 1401/1402) and outputs (e.g., notifications 1408) may utilize a cloud 1413 or the like, which may perform or support two way communications with the components of the network notification system. Further, the cloud 1413 may perform two way communications with any other smart devices 1403 that a user may have (e.g., smartphone, tablet, etc.), through which the user may access the cloud interfaces. Even further, the cloud 1413 may perform two way communication with medical professionals and third-party systems 1406 (e.g., emergency medical record (EMR) systems, disease management systems, genomic/genetic platforms physicians/healthcare professionals, patient vitals tracking devices/systems, and quantified-self devices/systems).

The cloud 1413 may use prioritized buffering and transmission to ensure non-redundant data is transmitted first during any communication, and to ensure reliability when user devices have limited Internet access.

The cloud 1413 may deliver alert communications upon triggers including but not limited to scheduled dosing (including any dosing requirements, such as an instruction to take a drug with food), misuse (e.g., missed medication, overdose) and unsafe drug interactions (e.g., Drug A and Drug B cause stomach bleeding if consumed within 24 hours of each other), where alerts may be in any form (e.g., emails, text messages, notifications on a dispenser) and may travel to any device, including locally networked devices or devices within a firewall.

The cascading or escalating chain of notification inputs and outputs may operate in the following manner, which is provided by way of example and not of limitation. A particular user may have a notification state in the cloud which may escalate based on trigger events 1402 (e.g., mis-dosing); the following embodiments of notification states may exist: (Level 1) Normal state, user may receive notifications through devices and app notifications (Level 2) Upon missing a dose, user may receive text messages, emails, etc. (Level 3) Emergency state, for example upon overdosing or repeated missing of scheduled doses, user may receive phone call from human customer service agent and emergency contacts may be alerted.

All communications may be fully compliant with regulatory requirements, including but not limited to HIPAA, and may be encrypted with industry standard or industry leading cryptographic technologies, such as 256-bit Rijndael encryption. All communications may pass through cloud's system servers to ensure complete reliability and security.

The cloud 1413 may connect to social media portals to supplement user data with additional fields, e.g., favorite foods. The system may communicate with GPS towers, cells towers, Wi-Fi nodes, and other wireless access points to determine or triangulate a user's location.

The cloud 1413 may connect with healthcare professionals, prescription vendors, and insurers automatically upon prescription issuance or entry, potentially for order processing, drug shipment, and regulatory data filing, among other functions.

The cloud 1413 may pull data from multiple online databases and news sources (which may be part of the additional data 1411 of the system 1400) to find and push SKU-specific up-to-date news and alerts, including but not limited to drug recalls, updated drug interactions, updated drug warnings, and manufacturer warning letters. This may include recalls.

The cloud 1413 may require authorization (e.g., user privileges 1414) from users to unlock access to cloud features as well as identify users. Methods for authorization may include but are not limited to the following: type, touch, speech, facial/visual recognition, fingerprint recognition, or combinations of these. Users may authorize certain human or automated agents to view all or a specified part of their user data. Agents may include but are not limited to doctors, hospital systems. Users may authorize agents on an individual basis or by certain agent characteristics, including but not limited to doctor specialty, doctor experience with consumable indication, and hospital group. Users may authorize site administrators and customer service representatives to access their accounts for troubleshooting and development purposes. Users that are account owners may authorize other users (whether part of their account or not) to consume certain SKUs or use certain dispensers.

Security of EMRs and other healthcare data structures may be enabled via data licensing and incremental digital signatures.

The cloud 1413 may provide dispensable unit usage trend identification via an analytics engine, e.g., for (1) input to medical professionals and systems, (2) warnings/recommendations based on recognized patterns and medical input, (3) on demand data/visuals for users, and (4) modification of pricing and supply chain (e.g. contract and internal manufacturing) of consumable products.

E-commerce backend may exist for auto-replenishing of containers via automatically triggered orders (when detecting containers are near empty), order queuing, dose queuing and replacement of prescription filling process by connecting users, healthcare professionals, and prescription vendors.

The cloud 1413 may provide storage, in a distributed database, of a user's data, item data, medical professional/system data listed above, and other data as appropriate, as well as hosting for additional content (including but not limited to blogs, user forums, site-specific media and content). User data in the cloud layer may be redundant with user data on cartridges or the like, and the cloud can perform conflict resolution as necessary. The cloud may cache frequently accessed user data for quick transmission to cartridges or the like.

Access to the cloud 1413 may be provided to third parties via a documented application programming interface (API). The API may allow access to evolving subset of full cloud functionality. Similarly, third party APIs may be used by the system to bring third party devices, networks, and ecosystems into the connected network and functionality of the dispensable unit system.

Customers may purchase a preset (for example "Family with children" preset) cartridge or the like. For preset products, the cloud may automatically configure the vanilla product to a particular preset based on the unique product ID and the associated product purchase information from the user.

Still more generally, a variety of fixed and distributed infrastructures may be usefully employed with system components to provide value added services and augment operation of the system for an individual user. Thus, portions of the systems and methods described above may be implemented in the cloud, while other portions use local processing resources for a device, such as a computer, printer, camera, and the like coupled to a local area network shared with the components of the system. In another aspect, other network resources may be usefully combined with cloud-based services and local processing resources to provide various layers of functionality, knowledge sharing, redundancy, and speed. For example, while a cloud-based or other remote-hosted system may manage personal inventory by automatically ordering replacement cartridges at appropriate times, this may also be performed with a suitably programmed local computer that can read compliance data, cartridge status, and scheduling information from a components of the system and determine when replacement cartridges might be needed. A local reminder may then be presented to the user, or the computer may autonomously connect to the network and authorize or make corresponding purchases. Still more generally, a single user may wish to autonomously manage all dispensing activity, and the system may be configured as a closed system with no external network connectivity, or with limited network activity, e.g., to issue e-mail or text message alerts from the local computer. At the same time, each function described above may occur at any number of locations. For example, monitoring consumable units may be performed by a cartridge, by a clip, by a base, by a local computing device, by a dedicated remote server, or by a general purpose, cloud-based management system. Similarly various notification systems, monitoring functions, data storage functions, management and administration functions and the like may be distributed or centralized in various manners across available resources according to user preferences, security requirements, oversight required by health care professionals, data integrity requirements and so forth. All such variations are intended to fall within the scope of this disclosure, and not particular function, service, system component, sub-component, or communications interface or endpoint should be presumed to reside with any specific system element unless explicitly stated to the contrary or otherwise clear from the context.

External services 1407 may be "connected" to the system 1400 via hardware or software integration. The system may expose an API whereby a third party device or system can, via its communication interface (including but not limited to Wi-Fi, Ethernet, WiMAX, 3G cellular and 4G-LTE), may send and receive instructions to/from a particular web address (according to, for instance, a RESTful API defined by the system) that may indicate one of the following states (but not limited to them): trigger occurrence on the side of the external service, authentication/authorization success or failure, readiness to accept/send communications to/from the system or not.

Notifications 1408 in this system 1400 may be tied to user accounts. There may be multiple levels of user functionality, illustratively one for administrators, professionals and caretakers ("admins"), and one for all other users. Admins may have access to all or a subset of user accounts, depending on their user privileges 1414, and in accordance with regulatory restrictions, including but not limited to HIPAA.

External services 1407 may be linked to individual users, or to multiple users. For instance, an administrator may be able to receive notifications 1408 to their personal external services 1407 (that function as outputs to the system 1400) based on triggers 1401 from external services 1407 (e.g., fall detectors) that belong to several elderly patients. Furthermore, a second non-administrator user may be able to receive notifications 1408 for a first non-administrator user (e.g., a patient) assuming that they are set up as such and are sufficiently privileged within the system 1400.

In an embodiment, the dispenser-notification system 1400 may interact with a third party tracking system or set of tracking rules (collectively referred to herein as "tracking mechanisms" 1415) for controlled substances, such as risk evaluation and mitigation strategies (REMS). This tracking mechanism 1415 may be centralized (for instance at a government agency) or distributed across several service providers or guideline-setters. A "controlled substance" may include a dispensable unit that poses some risk to humans or to the environment if used indiscriminately, or at the incorrect time/frequency, or in the incorrect combination, and may or may not be regulated by a regulatory body or government. Controlled substances may be present inside the dispenser, and dispensing-actions would refer to the dispensing of such controlled substances.

The dispenser-notification system 1400 may use such tracking mechanisms 1415 as inputs, whereby rules defined by the tracking mechanism 1415 define triggers 1401 in the dispenser-notification system, and whereby events 1402 occurring on the end of the tracking mechanism 1415 may activate triggers 1401 in the dispenser-notification system 1400.

The dispenser-notification system 1400 may use incorporate such tracking mechanisms' rules and events into its processing and analysis as described earlier. Particular analyses may identify dose conflicts or illegal or high-risk usage of particular controlled substances or combinations thereof.

The dispenser-notification system 1400 may use such tracking mechanisms 1415 as outputs, whereby communications are sent to the tracking mechanisms 1415 based on triggers 1401 activated at the system 1400 and processing is done by the system 1400. Such communications may have a particular content (e.g., notifications 1408 with specific content), which may be defined as described earlier for the system 1400, and may include machine instructions or human-readable reports. Particular outputs may include machine instructions to trigger an audit at a regulatory body (potentially via the external tracking mechanism 1415) and alert a manufacturer of a high-risk controlled substance usage event 1402 at a dispenser.

Based on its user database (which may be internal or within the cloud 1413), the dispenser-notification system 1400 may tie particular dispensing-actions or doses of controlled substances to specific users, defined user groups or dynamic user populations (including but not limited to groups defined based on usage and based on demographic).

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A device comprising:
   a container;
   a retrieval arm;
   a positioner coupled to the retrieval arm and actuatable to move the retrieval arm within the container;
   a sensor configured to measure a signal indicative of a level of dispensable units in the container, wherein the signal indicative of the level of the dispensable units is indicative of the force exerted by the retrieval arm on the container; and
   a controller in communication with the positioner and the sensor, the controller configured to receive, from the sensor, the signal indicative of the level of the dispensable units in the container, and to actuate the positioner to move the retrieval arm within the container according to a sequence of retrieval attempts, each retrieval attempt corresponding to a different two-dimensional pattern within a horizontal plane through the container, and each retrieval attempt carried out at a depth of the container based at least in part on the signal indicative of the level of the dispensable units in the container.

2. The device of claim 1, wherein the signal indicative of the level of the dispensable units is indicative of the weight of the dispensable units in the container.

3. The device of claim 1, wherein the sensor includes a strain gauge.

4. The device of claim 1, wherein the controller is further configured to actuate the positioner to move the retrieval arm, between unsuccessful retrieval attempts, by a retreat margin in a direction away from the level of the dispensable units in the container.

5. The device of claim 4, wherein the retreat margin is based on the signal indicative of the level of the dispensable units in the container.

6. The device of claim 1, wherein the container includes a bottom surface having at least one sloped portion.

7. The device of claim 1, wherein the retrieval arm includes a tube and a nib, the tube defining a hollow core, the nib coupled to the tube, and the nib defining an opening in fluid communication with the hollow core.

8. The device of claim 7, further comprising a vacuum source in fluid communication with the tube, the vacuum source controllable to apply a vacuum force through the hollow core to the nib.

9. A method comprising:
  measuring a signal indicative of a level of dispensable units in a container, wherein the signal indicative of the level of the dispensable units in the container corresponds to weight of the dispensable units in the container;
  moving a retrieval arm within the container according to a sequence of retrieval attempts of the dispensable units, each retrieval attempt associated with a different two-dimensional pattern within a horizontal plane through the container; and
  selectively adjusting a depth of each retrieval attempt within the container based at least in part on the signal indicative of the level of dispensable units in the container.

10. The method of claim 9, wherein measuring the signal indicative of the level of the dispensable units in the container includes measuring a response of a strain gauge in mechanical communication with the container.

11. The method of claim 9, wherein moving the retrieval arm within the container according to the sequence of retrieval attempts includes moving the retrieval arm by at least a predetermined distance within the horizontal plane.

12. The method of claim 11, wherein the predetermined distance is greater than half of a width of the retrieval arm.

13. The method of claim 9, wherein moving the retrieval arm within the container according to the sequence of retrieval attempts includes moving the retrieval arm in a random direction within the horizontal plane.

14. The method of claim 9, wherein moving the retrieval arm within the container according to the sequence of retrieval attempts includes moving the retrieval arm progressively toward or away from a perimeter of the container.

15. The method of claim 9, further comprising moving the retrieval arm, between unsuccessful retrieval attempts, by a retreat margin in a direction away from the level of the dispensable units in the container.

16. The method of claim 15, wherein the retreat margin is based on the signal indicative of the level of the dispensable units in the container.

17. The method of claim 9, further comprising applying a vacuum force to an end portion of the retrieval arm moving through the container during the sequence of retrieval attempts.

18. A method, comprising:
  measuring a signal indicative of a level of dispensable units in a container, wherein the signal indicative of the level of the dispensable units in the container corresponds to force of a retrieval arm on the containers;
  moving a retrieval arm within the container according to a sequence of retrieval attempts of the dispensable units, each retrieval attempt associated with a different two-dimensional pattern within a horizontal plane through the container; and
  selectively adjusting a depth of each retrieval attempt within the container based at least in part on the signal indicative of the level of dispensable units in the container.

* * * * *